US00RE37933E

(19) United States

(12) Reissued Patent

Branellec et al.

(10) Patent Number: US RE37,933 E

(45) Date of Reissued Patent: Dec. 10, 2002

(54) VIRAL VECTORS AND THEIR USE FOR TREATING HYPERPROLIFERATIVE DISORDERS, IN PARTICULAR RESTENOSIS

(75) Inventors: Didier Branellec, Brie-Comte-Robert (FR); Kenneth Walsh, Carlisle, MA (US); Jeffrey M. Isner, Weston, MA (US); Patrice Denefle, Saint Maur (FR)

(73) Assignee: Case Western Reserve University, Cleveland, OH (US)

(21) Appl. No.: 09/740,876

(22) Filed: Dec. 21, 2000

Related U.S. Patent Documents

Reissue of:

(64) Patent No.: 5,851,521
Issued: Dec. 22, 1998
Appl. No.: 08/723,726
Filed: Sep. 30, 1996

U.S. Applications:

(63) Continuation-in-part of application No. PCT/US96/04493, filed on Mar. 28, 1996.

(30) Foreign Application Priority Data

Mar. 31, 1995 (FR) ..... 95 04234

(51) Int. Cl.[7] ..... A61K 35/76; A61K 48/00; C12N 15/86; C12N 15/63

(52) U.S. Cl. ..... 424/93.2; 435/456; 435/320.1; 435/325; 435/375; 514/44; 536/23.5

(58) Field of Search ..... 424/93.2; 514/44; 435/320.1, 325, 375, 456; 536/23.1, 23.5

(56) References Cited

U.S. PATENT DOCUMENTS

| | | | | |
|---|---|---|---|---|
| 4,797,368 | A | 1/1989 | Carter et al. | 435/320 |
| 4,861,719 | A | 8/1989 | Miller | 435/236 |
| 5,139,941 | A | 8/1992 | Muzyezka et al. | 435/172.3 |
| 5,252,479 | A | 10/1993 | Srivastava | 435/235.1 |

FOREIGN PATENT DOCUMENTS

| | | |
|---|---|---|
| EP | 185 573 | 6/1986 |
| EP | 488 528 | 10/1991 |
| EP | 178 220 | 1/1992 |
| EP | 453 242 | 8/1996 |
| WO | WO 90/02806 | 3/1990 |
| WO | WO 91/18088 | 11/1991 |
| WO | WO 93/09239 | 5/1993 |
| WO | WO 94/11506 | 5/1994 |
| WO | WO 94/12649 | 6/1994 |
| WO | WO 94/26914 | 11/1994 |
| WO | WO 94/28152 | 12/1994 |
| WO | WO 94/28938 | 12/1994 |
| WO | WO 95/02697 | 1/1995 |
| WO | WO 95/23161 | 8/1995 |

OTHER PUBLICATIONS

Beard et al., "*Transcription Mapping of Mouse Adenovirus Type 1 Early Region 3*," Virology, vol. 175, pp. 81–90 (1990).

Bender et al., "*Evidence That the Packaging Signal of Moloney Murine Leukemia Virus Extends into the gag Region*," Journal of Virology, vol. 61 No. 5, pp. 1639–1646 (1987).

Berkner, "*Development of Adenovirus Vectors for the Expression of Heterologous Genes*," Biotechniques, vol. 6, pp. 616–629 (1988).

Bernstein et al., "*Gene Transfer with Retrovirus Vectors*," Genetic Engineer, vol. 7, pp. 235–261 (1985).

Biro et al., "*In Vitro Effects of a Recombinant Toxin Targeted to the Fibroblast Growth Factor Receptor on Rat Vascular Smooth Muscle and Endothelial Cells*," Circulation Research, vol. 71 No. 3, pp. 640–645 (1992).

Brancolini et al., "*Phosphorylation of the Growth Arrest–specific Protein gas2 is Coupled to Actin Rearrangements During Go G1 Transition in NIH 3T3 Cells*," Journal of Cell Biology, vol. 124 No. 5, pp. 743–756 (1994).

Branellec et al., "*A Recombinant Adenovirus Encoding gax can Efficiently Block Vascular Smooth Muscle Cell Proliferation*," Circulation, Supplement vol. 92 No. 8, Abstract 3041, pp. 1634 (1995).

Brinster et al., "*Introns Increase Transcriptional Efficiency in Transgenic Mice*," Proc. Natl. Acad. Sci. USA, vol. 85, pp. 836–840 (1988).

Casscells et al., "*Elimination of Smooth Muscle Cells in Experimental Restenosis: Targeting of Fibroblast Growth Factor Receptors*," Proc. Natl. Acad. Sci. USA, vol. 89, pp. 7159–7163 (1992).

Coccia et al., "*Regulation and Expression of a Growth Arrest–specific Gene (gas5) During Ggrowth, Differentiation, and Development*," Molecular & Cellular Biology vol. 12 No. 8, pp. 3514–3521 (1992).

Cowled et al., "*Expression of Growth Arrest–specific (gas) Genes in Senescent Murine Cells*," Experimental Cell Research, vol. 211, pp. 197–202 (1994).

Del Sal et al., "*The Growth Arrest–specific Gene, gas1, is Involved in Growth Suppression*," Cell, vol. 70, pp. 595–607 (1992).

Ferrero et al., "*Estrogen–regulated Expression of a Growth Arrest Specific Gene (gas–1) in Rat Uterus*," Cell Biology International, vol. 17 No. 9, pp. 857–862 (1993).

Ferrero et al., "*Expression of a Growth Arrest Specific Gene (gas–6) During Liver Regeneration: Molecular Mechanisms and Signalling Pathways*," Journal of Cellular Physiology, vol. 158, pp. 263–269 (1994).

Gehring et al., "*Homeodomain–DNA Recognition*," Cell, vol. 78, pp. 211–223 (1994).

Gorski et al., "*Molecular Cloning of a Diverged Homeobox Gene that is Rapidly Down–regulated During the G0/G1 Transition in Vascular Smooth Muscle Cells*," Molecular & Cellular Biol., vol. 13, No. 6, pp. 3722–3733 (1993).

(List continued on next page.)

*Primary Examiner*—Scott D. Priebe

(74) *Attorney, Agent, or Firm*—Finnegan, Henderson, Farabow, Garrett & Dunner LLP

(57) ABSTRACT

The present invention relates to replication defective recombinant viruses which contain at least one inserted gene encoding all or part of the protein GAX or of a variant of this protein, and to their therapeutic use, in particular for treating post-angioplastic restenosis.

50 Claims, 25 Drawing Sheets

OTHER PUBLICATIONS

Gorski et al., "*Mitogen–responsive Nuclear Factors that Mediate Growth Control Signals in Vascular Myocytes*," Cardiovascular Research, vol. 30, pp. 585–592 (1995).

Graham et al., "*Characteristics of a Human Cell Line Transformed by DNA from Human Adenovirus Type 5*," J. Gen. Virol., vol. 36, pp. 59–72 (1977).

Graham et al., "*Covalently Closed Circles of Human Adenovirus DNA and Infections*," The EMBO Journal, vol. 3 No. 12, pp. 2917–2922.

Isner et al., "*Gene Therapy for Arterial Disease*," The Lancet, vol. 344, pp. 1653–1654 (1994).

Jackman et al., "*Genotoxic Stress Confers Preferential and Coordinate Messenger RNA Stability on the Five gadd Genes*," Cancer Research, vol. 54, pp. 5656–5662 (1994).

Krumlauf, "*Hox Genes in Vertebrae Development*," Cell, vol. 78, pp. 191–201 (1994).

La Page et al., "*Molecular Cloning and Localization of the Human GAX Gene to 7p21*," Genomics, vol. 24, pp. 535–540 (1994).

Lawrence et al., "*Homeobox Genes: their Function in Drosphila Segmentation and Pattern Formation*," Cell, vol. 78, pp. 181–189 (1994).

Lemarchand et al., "*In Vivo Gene Transfer and Expression in Normal Uninjured Blood Vessels Using Replication–deficient Recombinant Adenovirus Vectors*." Circulation Research, vol. 72, pp. 1132–1138 (1993).

Levero et al., "*Defective and Nondefective Adenovirus Vectors for Expressing Foreign Genes in Vitro and in Vivo*," Gene, vol. 101, pp. 195–202 (1991).

March et al., "*8–methoxypsoralen and Longwave Ultraviolet Irradiation are a Novel Antiproliferative Combination for Vascular Smooth Muscle*," Circulation, vol. 87 No. 1, pp. 184–191 (1993).

March et al., "*Pharmokinetics of Adenoviral Vector–mediated Gene Delivery to Vascular Smooth Muscle Cells: Modulation by Poloxamer 407 and Implications for Cardiovascular Gene Therapy*," Hum. Gene Ther., vol. 6, pp. 41–53 (1995).

Marshall, "*Gene Therapy's Growing Pains*," Science, vol. 269, pp. 1050–1055 (1995).

McCormick, "*Human Gene Therapy: the First Round*," Bio/Technology, vol. 3 No. 8, pp. 689–693 (1985).

Miller et al., "*Targeted Vectors for Gene Therapy*," FASEB J., vol. 9, pp. 190–199 (1995).

Ohno et al., "*Gene Therapy for Vascular Smooth Muscle Cell Proliferation After Arterial Injury*," Science, vol. 265, pp. 781–784 (1994).

Pickering et al., "*Prevention of Smooth Muscle Cell Outgrowth From Human Atherosclerotic Plaque by a Recombinant Cytotoxin Specific for the Epidermal Growth Factor Receptor*," Journal of Clinical Investment, vol. 91, pp. 724–729 (1993).

Riessen et al., "*Prospects for Site–specific Delivery of Pharmacologic and Molecular Therapies*," J. Am. Coll. Cardiol., vol. 23, pp. 1234–1244 (1994).

Riessen et al., "*Percutaneous Arterial Gene Transfer Using Pure DNA Applied to a Hydrogel–coated Angioplasty Balloon*," Eur. Heart J., vol. 14, Abstract 590, 78 (1993).

Schneider et al., "*Genes Specifically Expressed at Growth Arrest of Mammalian Cells*," Cell, vol. 54, pp. 787–793 (1998).

Steg et al., "*Arterial Gene Transfer to Rabbit Endothelial and Smooth Muscle Cells Using Percutaneous Delivery of an Adenoviral Vector*," Circulation, vol. 9, No. 4, pp. 1648–1656 (1994).

Walsh et al., "*Cell Cycle Control by the gax Homeobox Protein in Vascular Smooth Muscle Cells*," Circulation, vol. 90, Abstract 3420, pp. 1635 (1994).

Weir et al., "*Gax is Rapidly Downregulated in Rat Carotid Arteries Following Balloon Injury: in Vivo Demonstration of a Growth–arrest Transcription Factor*," Circulation, vol. 90, Abstract 2747, pp. 1511 (1994).

Zahn et al., "*Induction of Cellular p53 Activity by DNA–damaging Agents and Growth Arrest*", Molecular & Cellular Biology, vol. 13 No. 7, pp. 4242–4250 (1993).

FIG. 17A
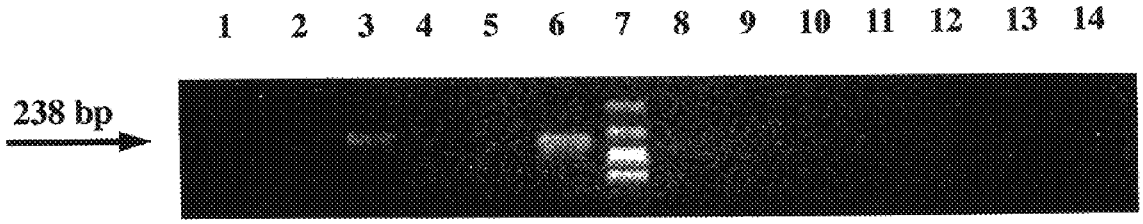
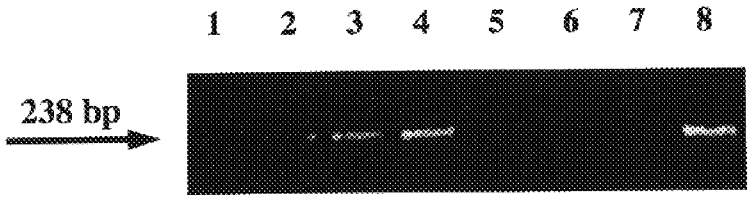
FIG. 17B

VIRAL VECTORS AND THEIR USE FOR TREATING HYPERPROLIFERATIVE DISORDERS, IN PARTICULAR RESTENOSIS

Matter enclosed in heavy brackets [ ] appears in the original patent but forms no part of this reissue specification; matter printed in italics indicates the additions made by reissue.

CROSS-REFERENCE TO RELATED APPLICATION

This application is a continuation-in-part of PCT/US96/04493, filed Mar. 28, 1996.

BACKGROUND OF THE INVENTION

1. Field of the Invention

The present invention is directed to methods and compositions for treating pathologies associated with hyperproliferative disorders. Among the hyperproliferative disorders which may be treated according to the invention are various tumors and cardiovascular diseases, such as vascular restenosis resulting from mechanical injury at an angioplasty site during treatment of an atheroscerotic lesion.

Atherosclerosis is a complex, polygenic disease which is defined in histological terms by deposits (lipid or fibrolipid plaques) of lipids and of other blood derivatives in blood vessel walls, especially the large arteries (aorta, coronary arteries, carotid). These plaques, which are more or less calcified according to the degree of progression of the atherosclerotic process, may be coupled with lesions and are associated with the accumulation in the vessels of fatty deposits consisting essentially of cholesterol esters. These plaques arc accompanied by a thickening of the vessel wall, hypertrophy of the smooth muscle, appearance of foam cells and accumulation of fibrous tissue. The atheromatous plaque protrudes markedly from the wall, endowing it with a stenosing character responsible for vascular occlusions by atheroma, thrombosis or embolism, which occur in those patients who are most affected. These lesions can lead to very serious cardiovascular pathologies such as infarction, sudden death, cardiac insufficiency, and stroke.

The technique of angioplasty has been developed to permit a non-surgical intervention of the atherosclerotic plaque. However, the treatment of an atherosclerotic lesion by angioplasty results very frequently (up to 50% of cases in some studies) in a restenosis following mechanical injury of the arterial wall A key event in this mechanism is the proliferation and migration of vascular smooth muscle cells (VSMC) from the media to the intima, as a result of the absence of protection and/or feedback control exercised by the endothelial cells of the intima.

Treatment of restenosis by administration of chemical or proteinaceous substances capable of killing vascular smooth muscle cells has been proposed. For example, psolaren derivatives, incorporated by proliferative cells and then sensitizing these cells to the action of light, have been used (March et al., 1993, Circulation, 87:184–191). Similarly, some cytotoxins consisting of a fusion protein between a plant or bacterial toxin fragment and a growth factor have also been used (Pickering et al., J. Clin. Invest., 1993, 91:724–729; Biro et al., 1992, Circ, Res., 71:640–645; Casscells et al., *Proc. Natl. Acad. Sci. USA*, 1992, 89:7159–7163). However, these treatments have many drawbacks, such as their low specificity, their indifferent efficacy; a considerable delay in acting and a potential toxicity. The present invention provides an effective, gene therapy approach for the treatment of hyperproliferative disorders, including restenosis.

2. Description of Related Art

Various genes have been isolated which are linked to the arrest of cell division. The gas (growth-arrest specific; gas 1–6) and gadd (growth-arrest and DNA damage-inducible; gadd34, gadd45 and gadd153) genes are strongly expressed in quiescent cells, that is cells which are blocked in the G0 phase of the cell cycle (Schneider et al., Cell 1988, 54; 787–793, Del Sal et al., Cell 1992, 12:3514–3521; Cowled et al., Exp.Cell.Res. 1994, 211:197–202; Brancolini and Schneider, J.Cell.Biol, 1994, 124:743–756; Zhan et al., Mol.Cell.Biol. 1993, 13:4242–4250; Jackman et al., Cancer Res. 54:5656–5662, 1994). In agreement with these findings on gene expression, microinjection of the gas-1 protein blocks the synthesis of DNA (Del Sal et al., Cell, 1992, 70:595–607). Conversely, the addition of growth factors such as PDGF (platelet-derived growth factor) or foetal calf serum decreases the expression of these genes in in-vitro models (Coccia et al. Mol.Cell.Biol. 1992, 12:3514–3521). This specificity of expression in relation to the state of cell proliferation also appears to have its counterpart in vivo. Thus, the gas-1 gene is strongly expressed in the rat uterus following ovariectomy (Ferrero and Cairo, Cell.Biol.Int. 1993, 17, 857–862). In this same animal model, treatment with oestrogeos results in a cell proliferation which is reflected, within the uterus, in an increase in the expression of the proto-oncogene c-myc and by a decrease in the expression of the gas-1 gene. Similarly, in a hepatic model of proliferation/regeneration, expression of the gas-6 gene is strongly reduced four hours after partial heptatectomy, i.e. in the period of transition from G0 to G1; this expression returns to normal, probably once division of the hepatocytes has been initiated (Ferrero et al. J.Cell.Physiol. 1994, 158:263–269).

Homeobox genes encode transcription factors which, at a cellular level, control growth, differentiation, and migration. The homeobox gene GAX (growth arrest-specific homeobox) is expressed in adult cardiovascular tissues and in muscular embryonic tissues. The GAX gene was initially identified in a cDNA library prepared from rat aorta. It encodes a protein of 303 amino acids. Its sequence has been characterized and its cDNA has been cloned (Gorski et al., Mol.Cell.Biol. 1993, 6, 3722–3733) The GAX homeobox gene is normally expressed in quiescent VSMCs and rapidly downregulated under conditions that induce VSMC dedifferentiation and proliferation. The GAX gene possesses certain properties which are similar to those of the gas and gadd genes, since it also appears to regulate the G0/G1 transition in the cell cycle. In the same way, the levels of GAX mRNA are decreased in the rat VSMCs by a factor of 10 after two hours of exposure to PDGF (Gorski et al., Mol.Cell.Biol. 1993, 6, 3722–3733). Expression of the GAX gene is therefore repressed during the VSMC mitogenic response. Gax expression is also rapidly down-regulated in vascular tissue immediately following balloon injury.

SUMMARY OF THE INVENTION

The present invention is directed to viral vectors comprising a GAX gene, compositions including the same, and using said composition for specifically arresting cell division. The GAX gene possesses properties which are particularly advantageous for use in the gene therapy of hyperproliferative disorders, in particular restenosis, by overexpression of the GAX gene in the vascular wall.

Methods of the invention comprise blocking proliferation of vascular smooth-muscle cells (VSMC) by in vivo delivery of a GAX gene in a viral vector, preferably replication defective recombinant adenoviral vectors.

The invention provides replication defective recombinant adenoviruses comprising at feast one inserted gene encoding all or part of a GAX protein or a variant thereof.

The invention provides methods for the treatment or prevention of a pathology linked to a hyperproliferative disorder, said method comprising administration of a replication defective recombinant adenovirus comprising at least one inserted gene encoding all or part of a GAX protein or a variant thereof.

The invention provides a method of treating restenosis comprising administering to a patient in need of such treatment a replication defective recombinant adenovirus comprising a GAX gene, in an amount effective to inhibit vascular smooth muscle cell proliferation and migration at a predetermined site. More preferably, the site is a site of mechanical injury to an arterial wall produced by treatment of an atherascterotic lesion by angioplasty.

The invention provides pharmaceutical compositions comprising one or more replication defective recombinant adenoviruses comprising at least one inserted gene encoding all or part of a GAX protein or a variant thereof.

These and other embodiments of the invention are discussed in detail below.

BRIEF DESCRIPTION OF THE DRAWINGS

FIG. 3A: VSMCs transfected with vector pCGN (absence of GAX insert)

FIG. 3B VSMCs transfected with vector pXL-CMW GAX$^{HA}$.

The VSMCs are counted 24 bows after having been treated with Ad-CMV-GAX (1000 pfu/cell) or with a control adenovirus (Ad-RSV-βGal, 1000 pfu,/cell). Cell growth is blocked (0.5% FCS) or stimulated (FCS 20%).

Figure 6:
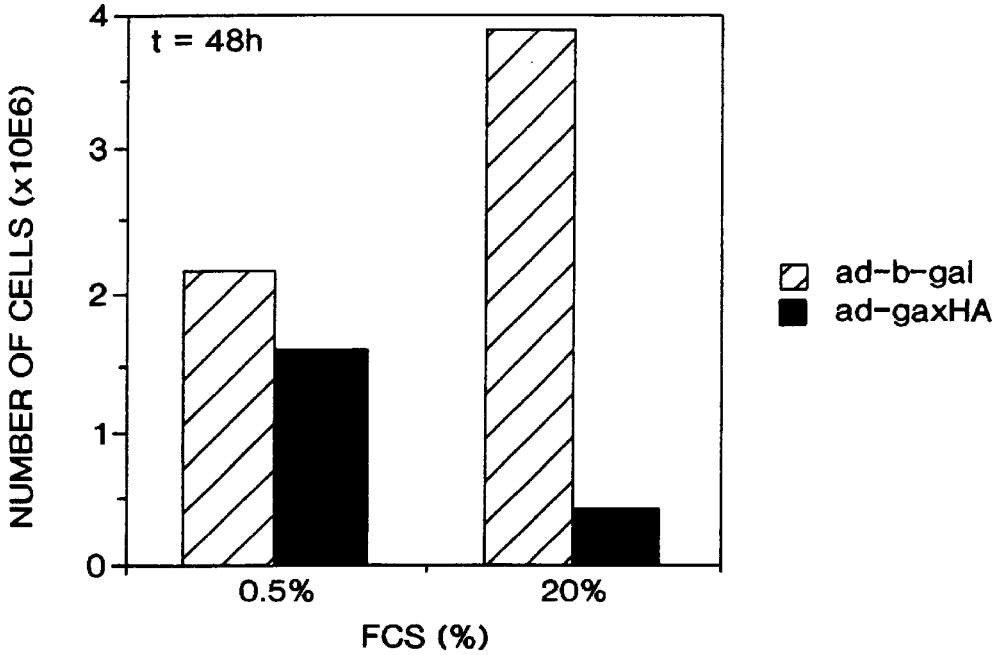

FIG. 6: Effect of Ad-CMV-GAX on the proliferation of VSMCs (t=48 hours)

The VSMCs are counted 48 hours after having been treated with Ad-CMV-GAX (1000 pfu/cell) or with a control adenovirus (AD-RSV Gal, 1000 pfu/cell). Cell growth is blocked (0.5% FCS) or stimulated (FCS 20%).

Figure 7A:
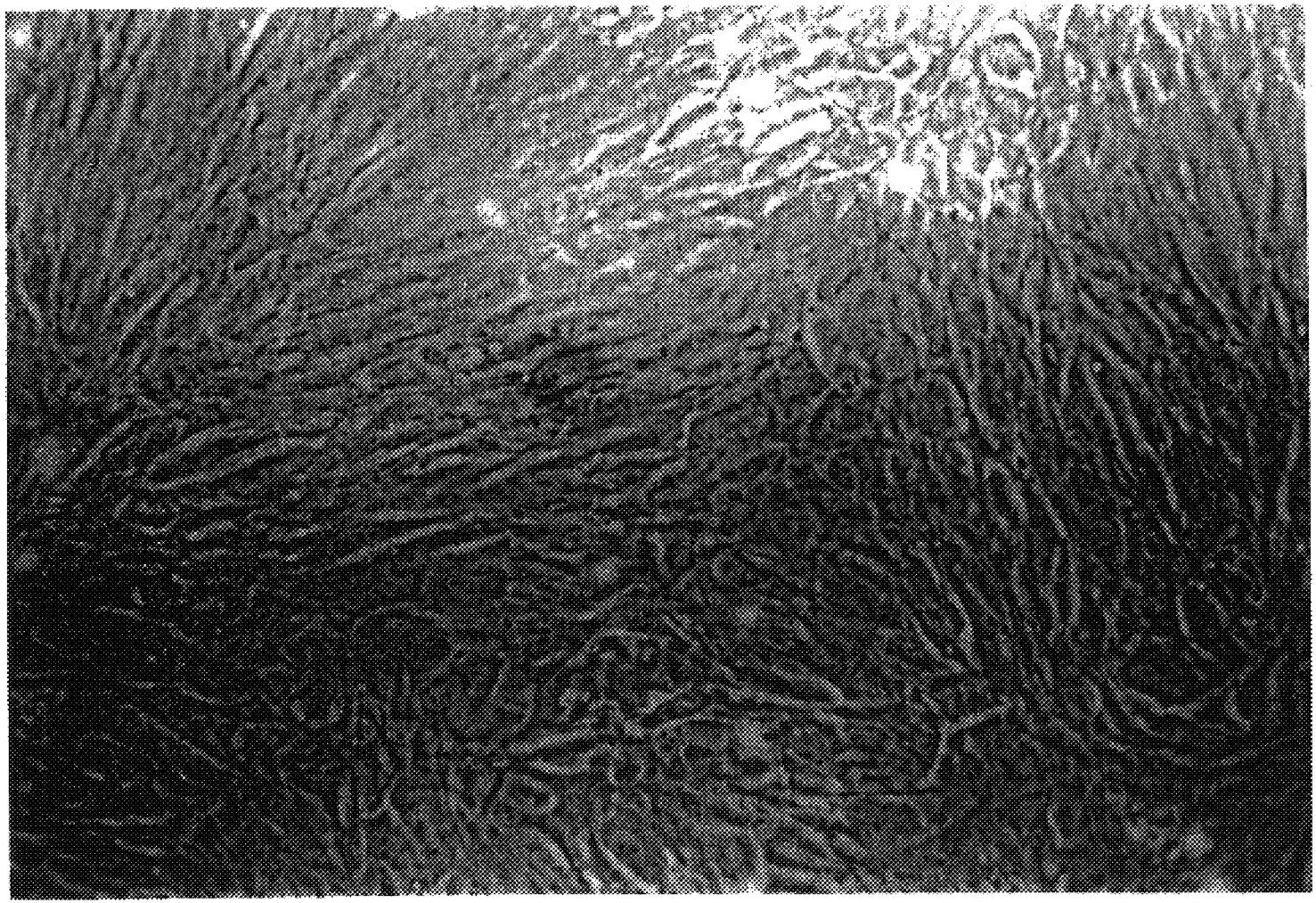
Figure 7B:
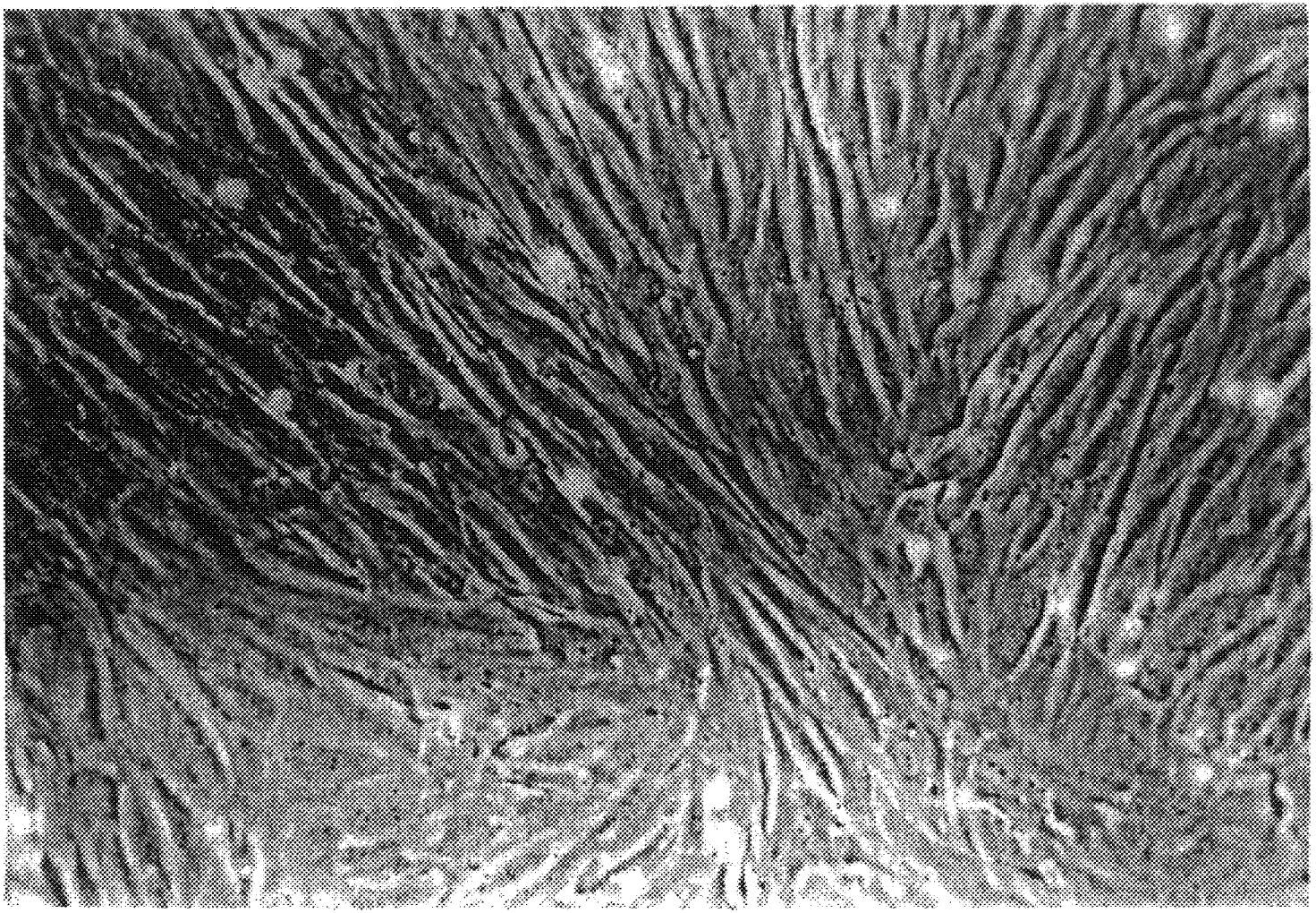
Figure 7C:
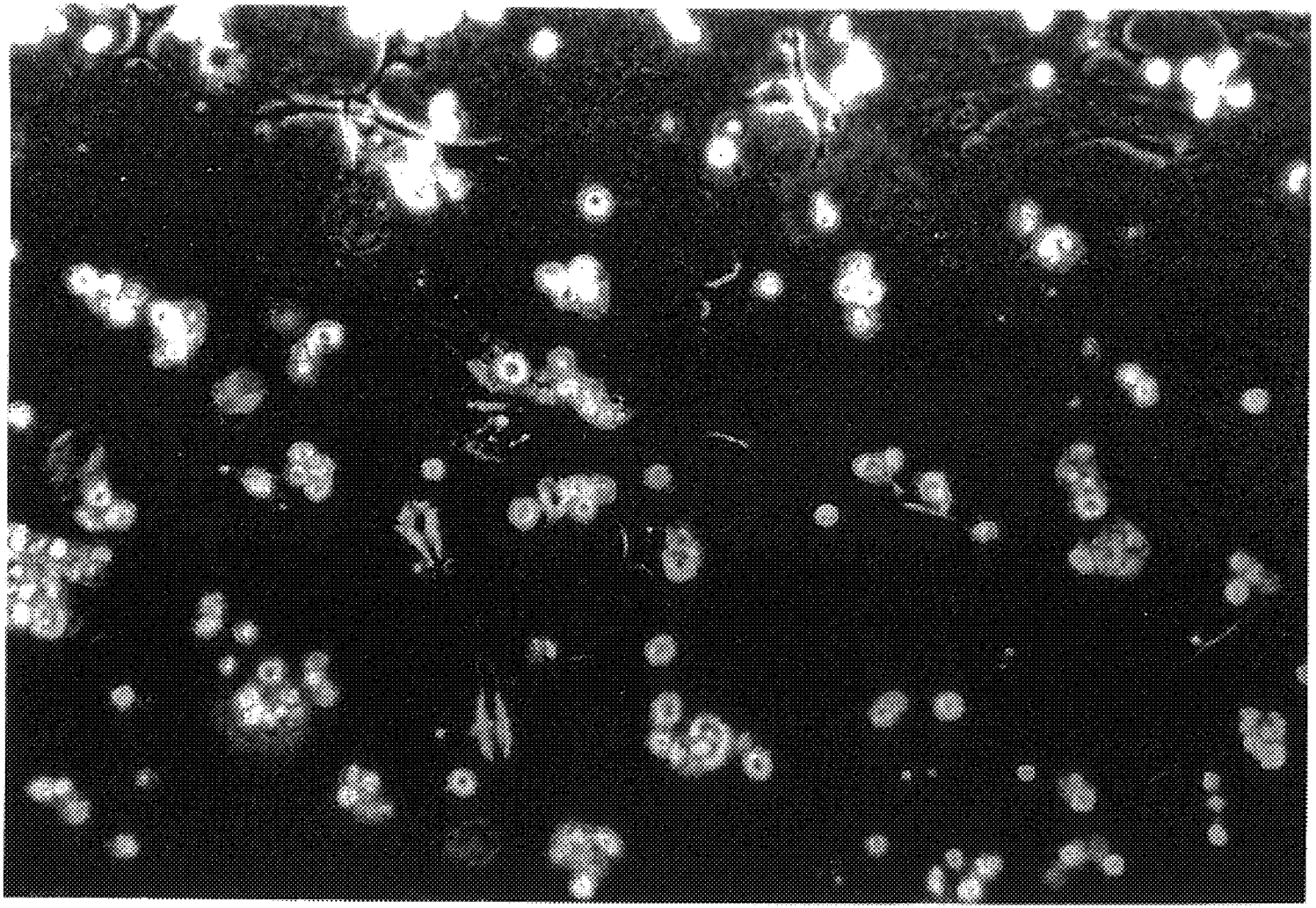

FIGS. 7A–7C: Effect of Ad-CMV-GAX on the viability of VSMCs which are incubated in the presence of foetal calf serum (FCS 20%), experimental conditions, cf. FIG. 6

FIG. 7A: cells which are not treated with adenovirus

FIG. 7B: cells which are treated with Ad-RSV Gal

FIG. 7C: cells which are treated with Ad-CMV-GAX

Figure 8A:
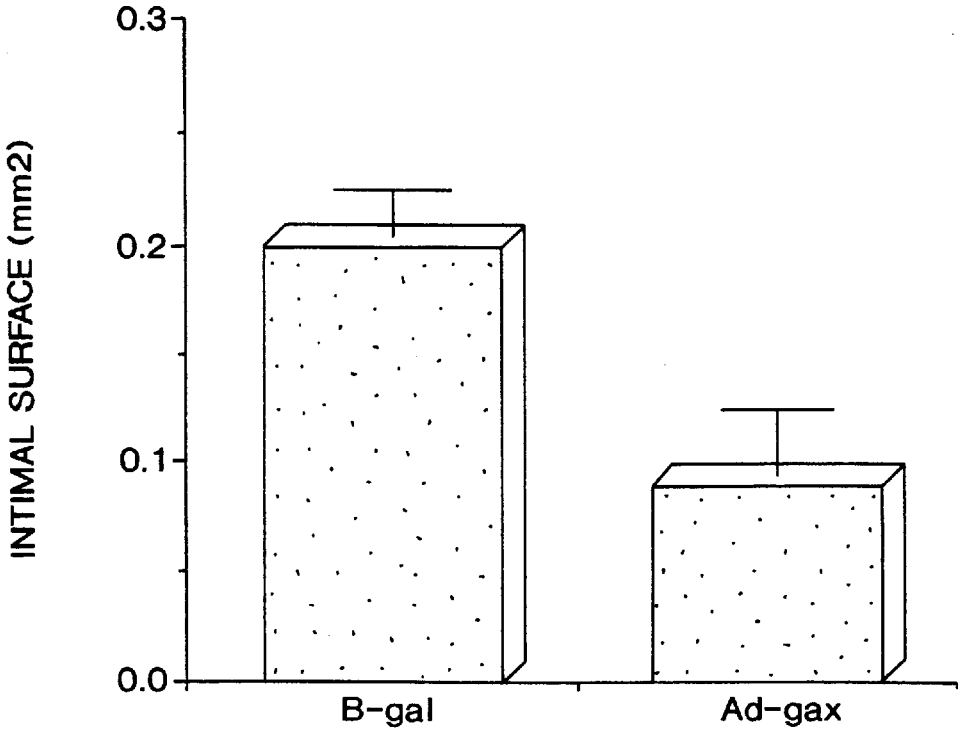
Figure 8B:
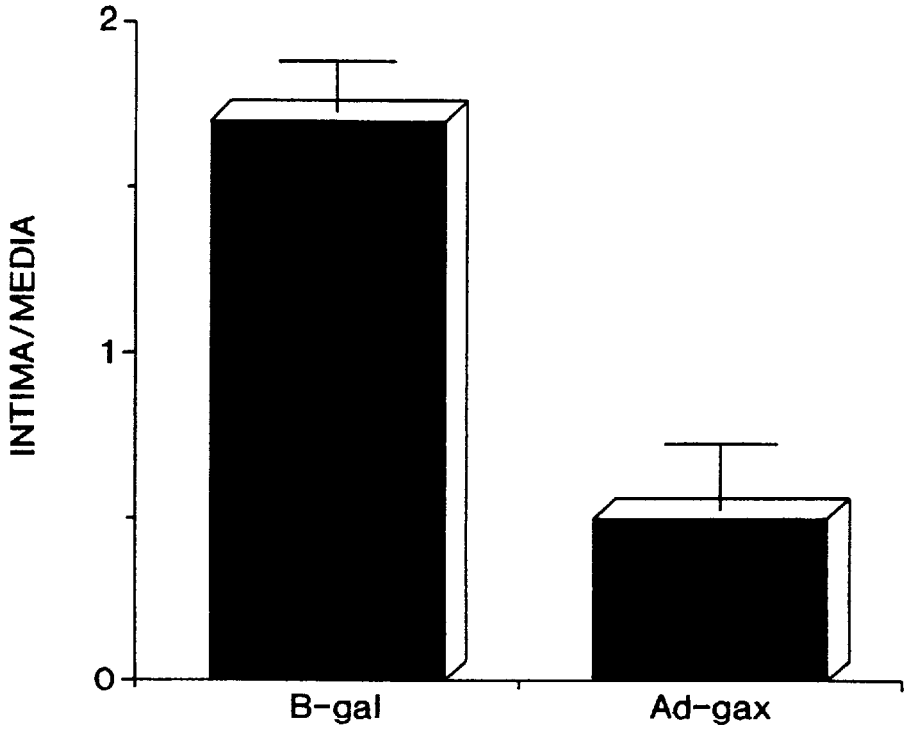
Figure 8C:
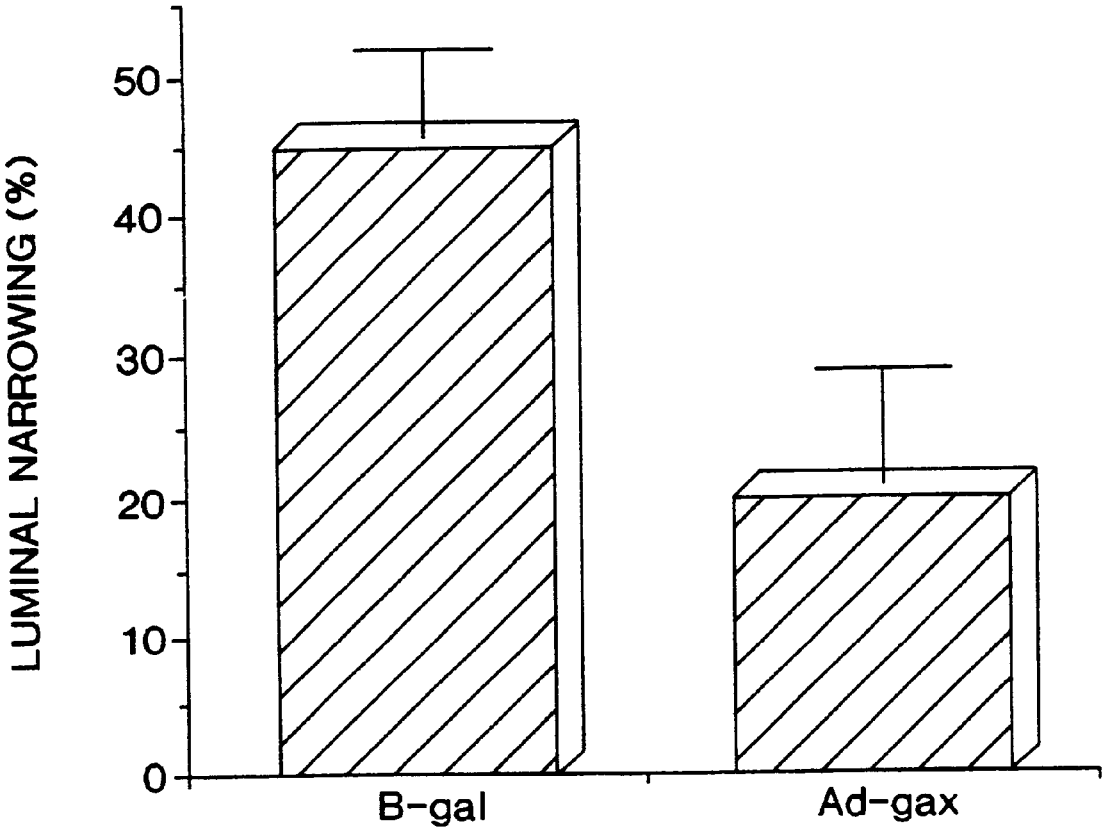

FIGS. 8A–8C: Effects of Ad-CMV-GAX and Ad-RSV βGal on rat carotid arteries following injury with a balloon catheter.

FIG. 8A: measurement of intimal surface area

FIG. 8B: measurement of the ratio of intima to media

FIG. 8C: measurement of luminal narrowing.

Figure 9A:
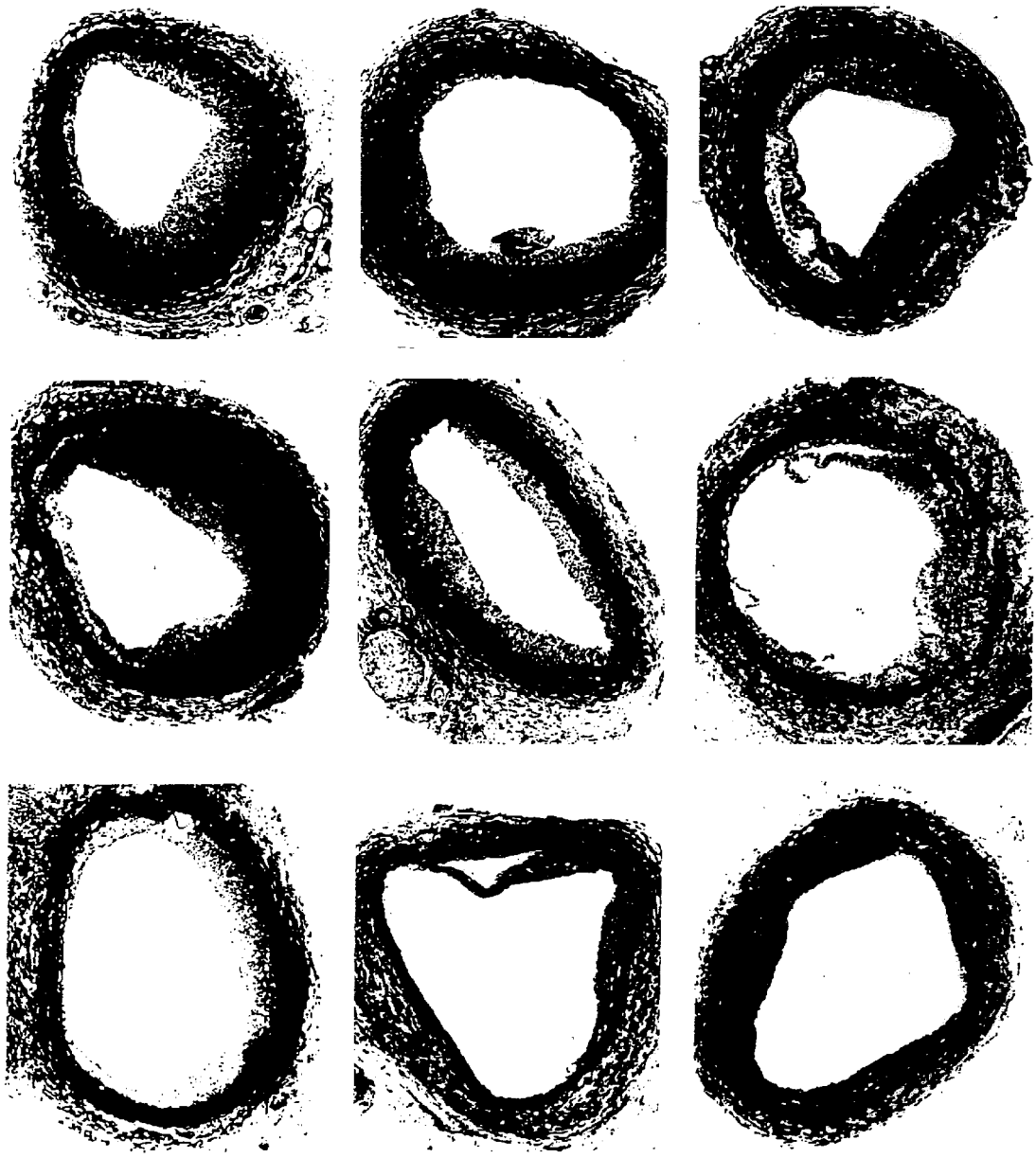
Figure 9B:
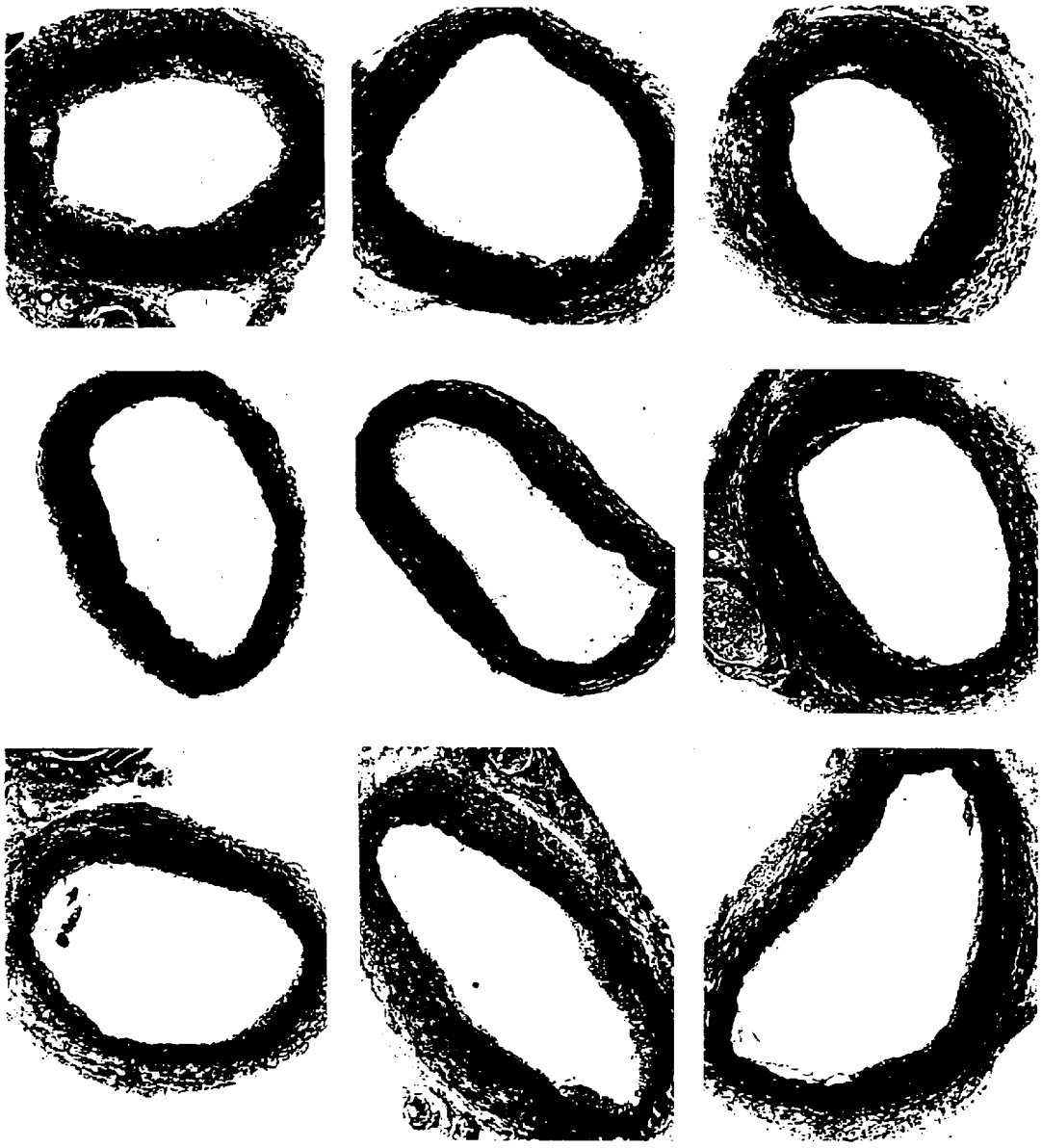
Figure 10A:
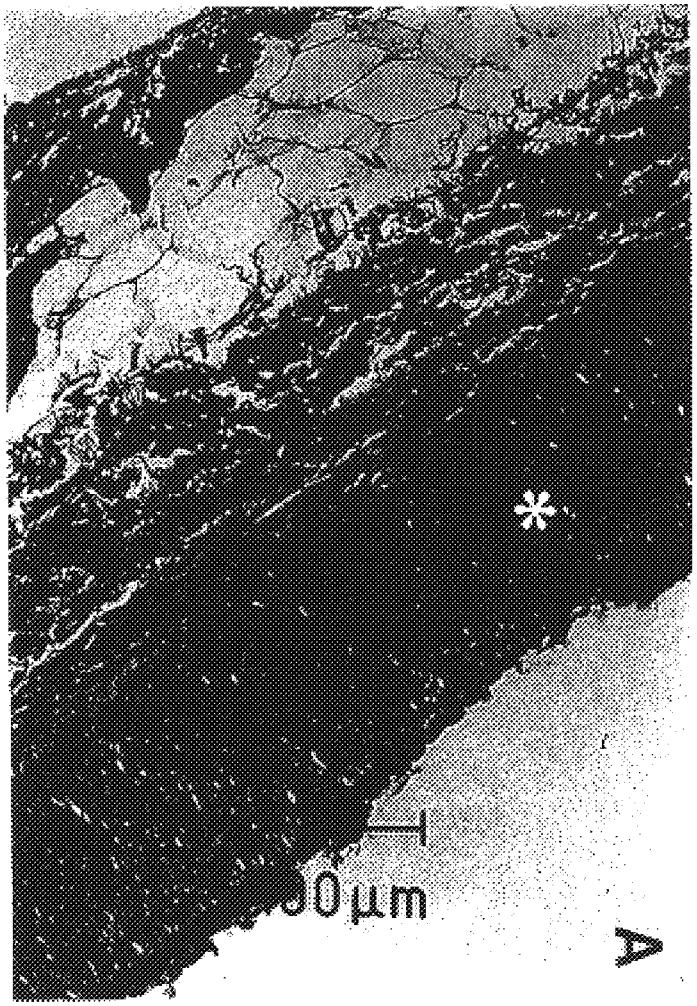
Figure 10B:
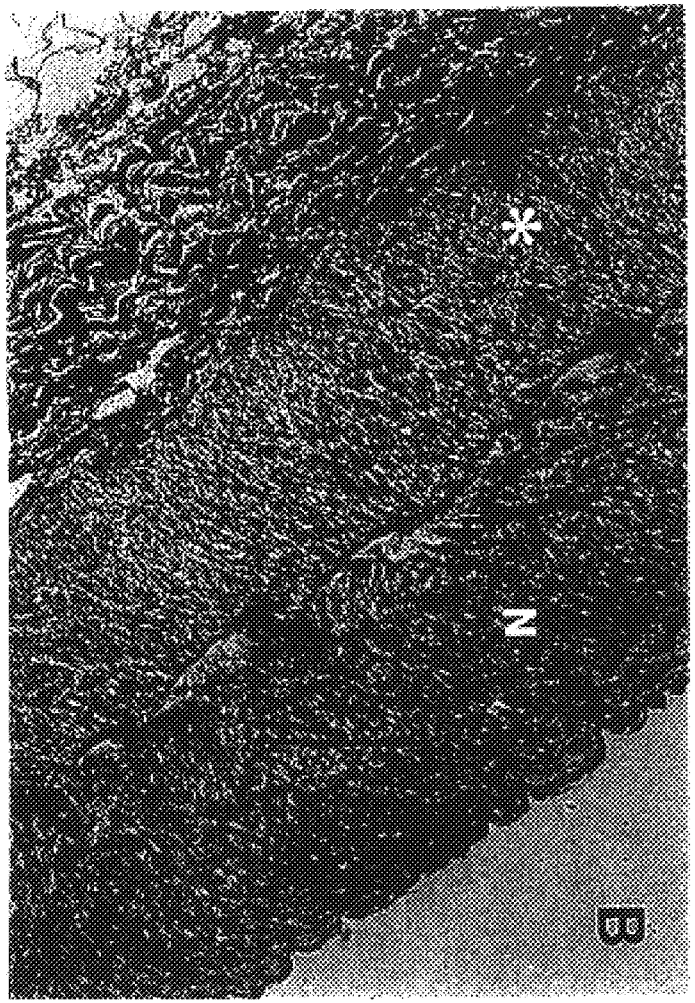
Figure 10C:
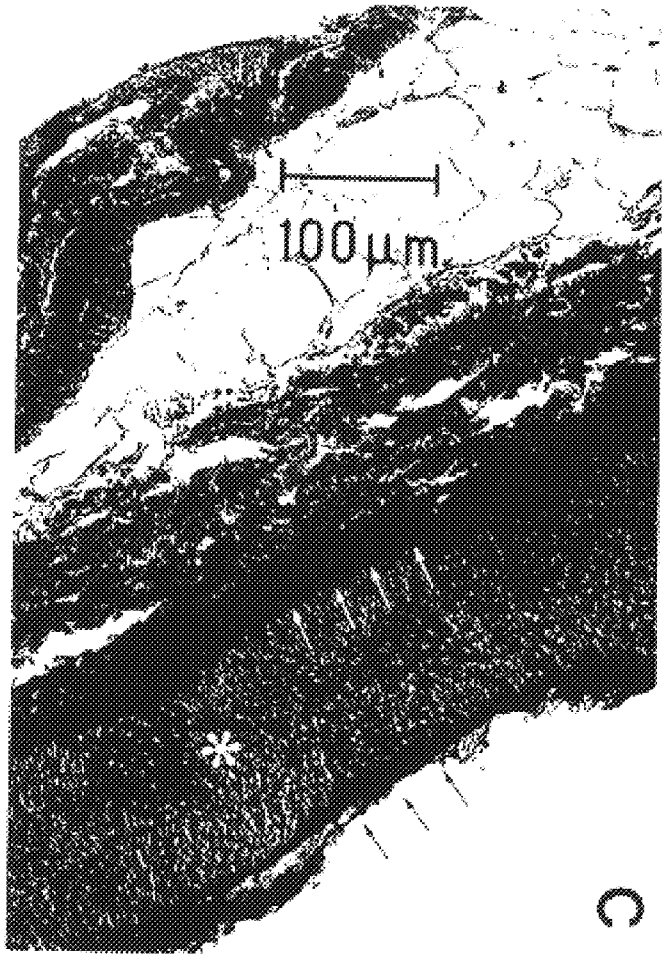
Figure 10D:
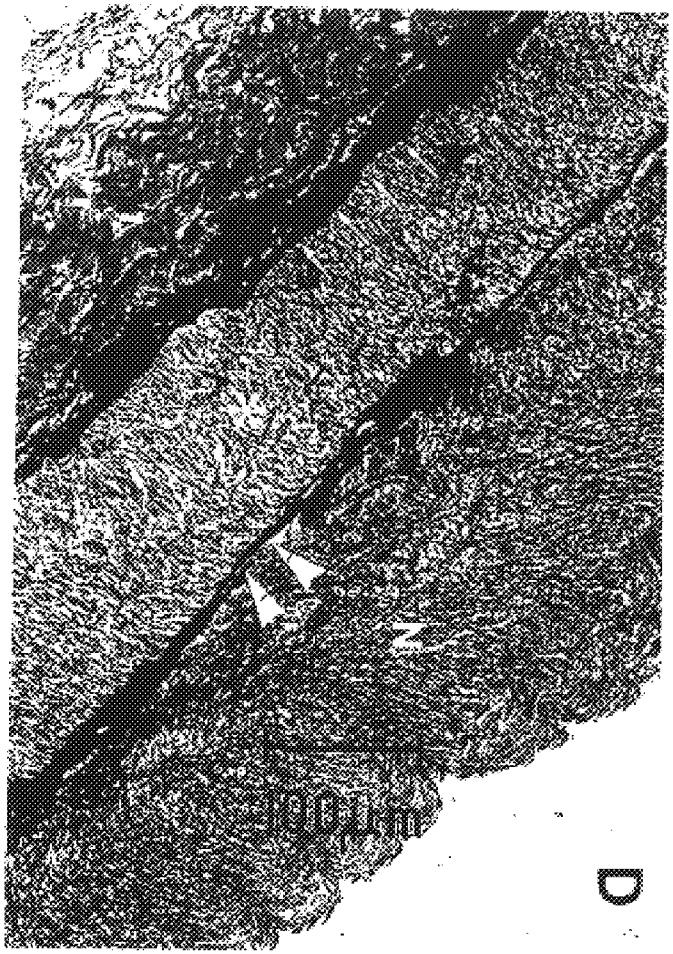

FIGS. 9A and 9B: Arterial cross sections of control and treated vessels

FIG. 9A: Ad-RSV-βGal treated control vessels

FIG. 9B: Ad-CMV-GAX treated vessels.

FIGS. 10A–10D: Ad-Gax infected vessels display less intimal hyperplasia. Representative longitudinal cross-sections of Ad-Gax (A & C) and Ad-βgal-infected (B & D) contralateral arteries from the same animal harvested 28 days after angioplasty. While neointima is limited in the Ad-Gax-infected vessel the controlateral Ad-βgal-infected vessel displayed a large neointima. A and B hematoxylin and eosin staining, C and D elastic trichrome staining. The arrowheads point to the internal and external lamina. N: neointima, Star: media, Bar=100 $\mu$m.

Figure 11B:
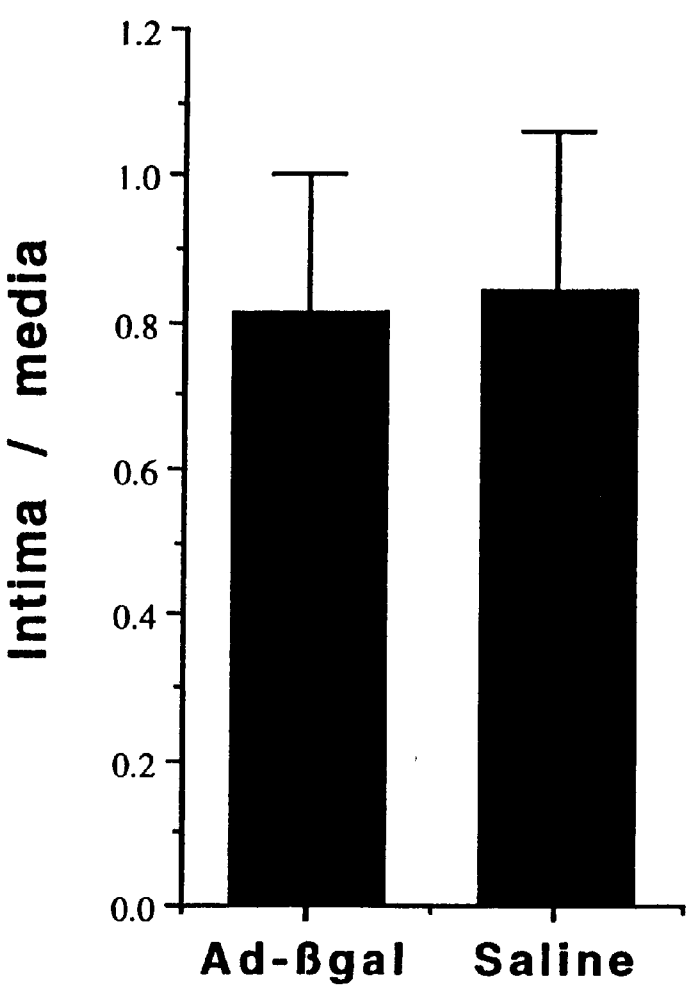
Figure 11A:
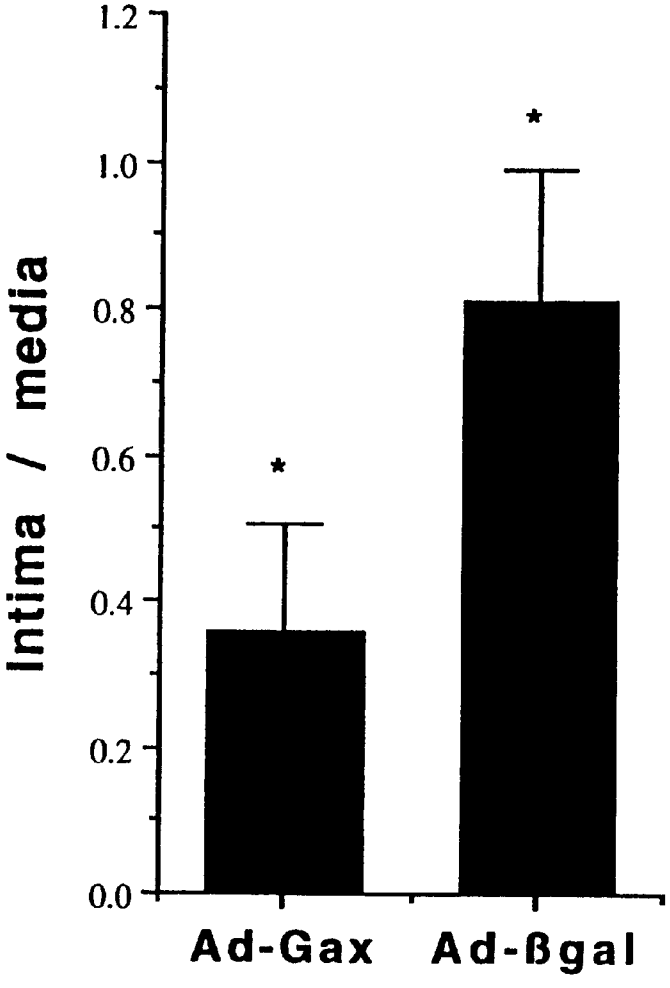
Figure 12A:
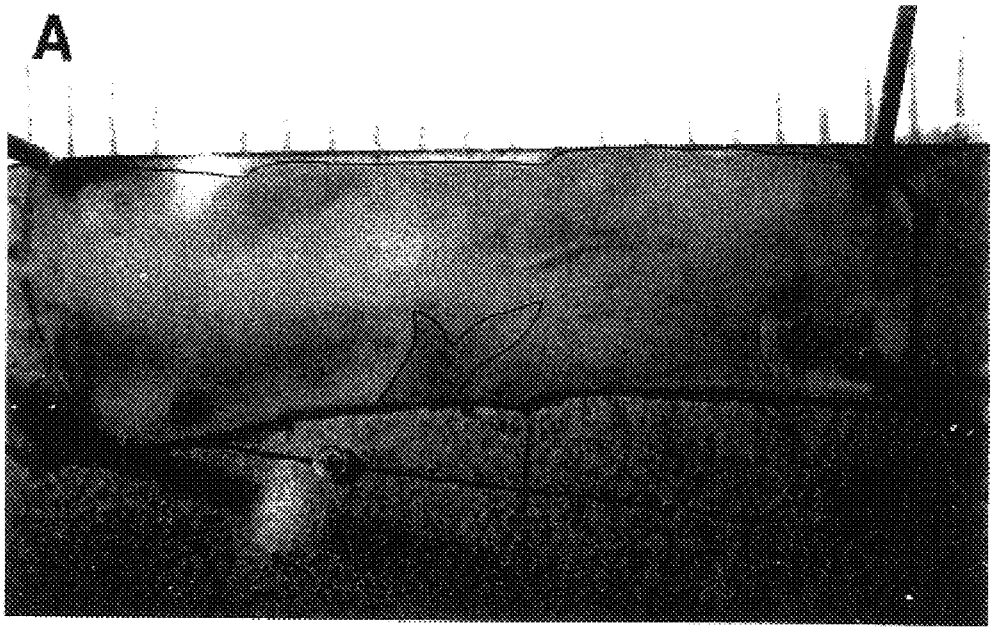
Figure 12B:
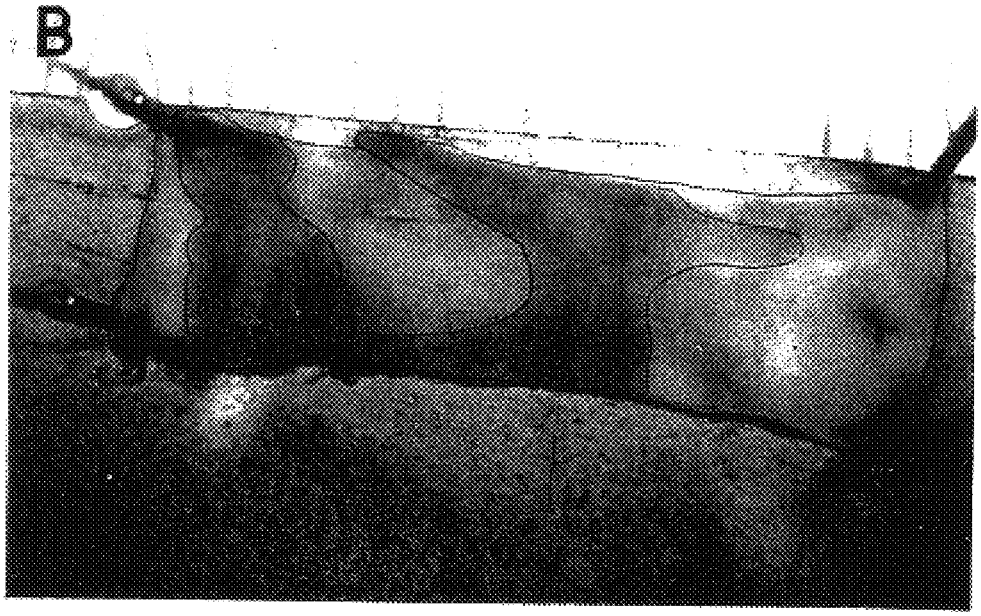
Figure 12C:
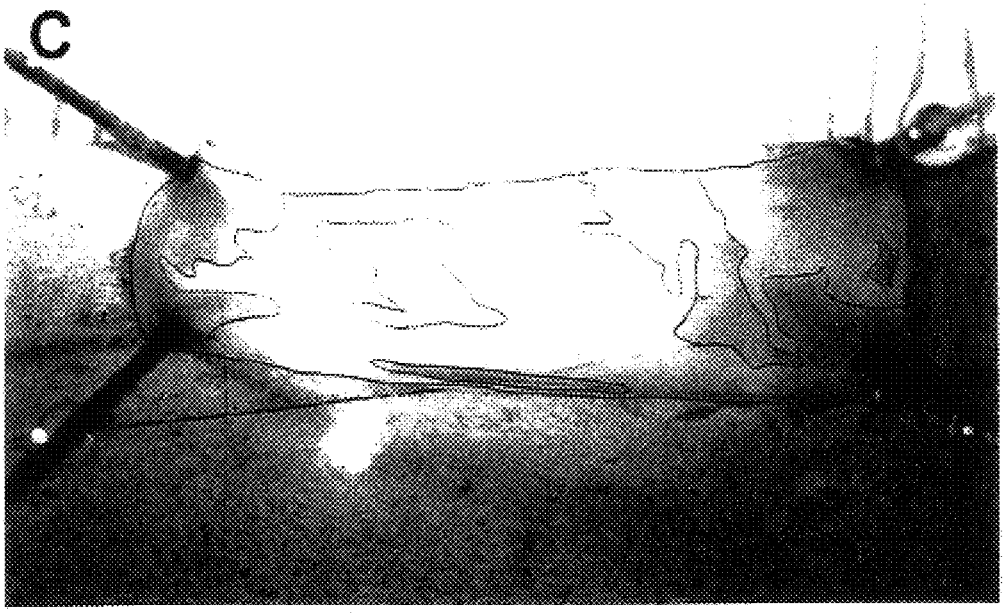
Figure 12D:
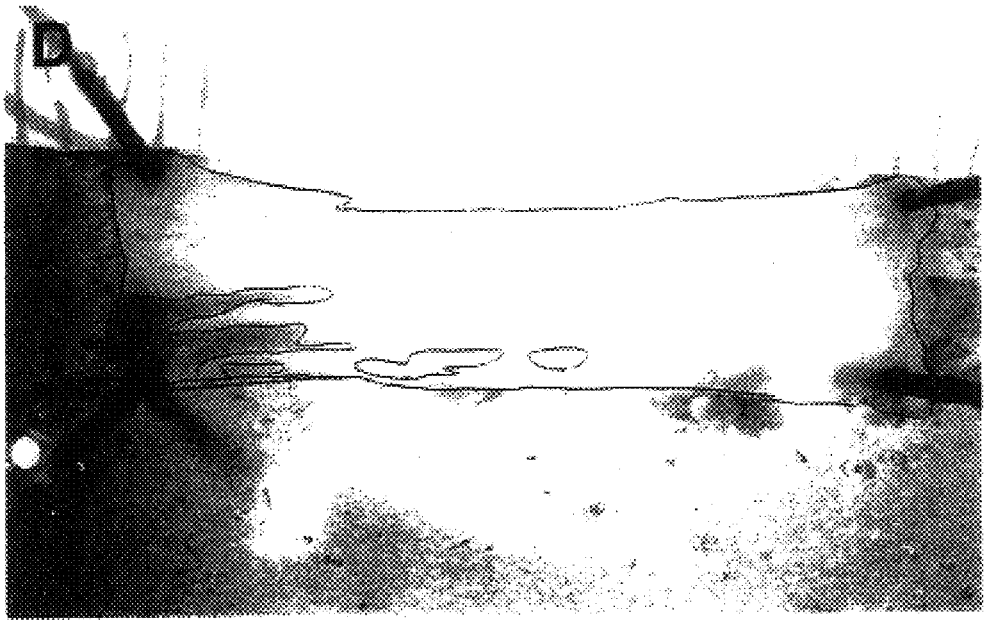

FIGS. 11A and 11B: Summary of ratios of intimal to medial areas in the Ad-Gax versus the Ad-β-gal and in the Ad-β-gal versus saline treated arteries. Results from quantitative morphologic analysis demonstrate that the Ad-Gax-treated arteries had I/M ratios that were 5096 less than that of the I/M ratios in the contralateral Ad-βgal-treated arteries ($p<0.02$). In contrast, no statistically significant differences occured between the Ad-βgal-treated and the contralateral saline-treated animals in the second group.

FIGS. 12A–12D: Representative photographs of planimetric analysis of Evans blue-stained Ad-Gax (FIGS. 12A and 12C) vs. contralateral Ad-β-gal (FIGS. 12B and 12D) treated arteries in 2 rabbits. Ad-Gax and Ad-βga-infected vessels display incomplete reendothelialization at 1 month.

Figure 13B:
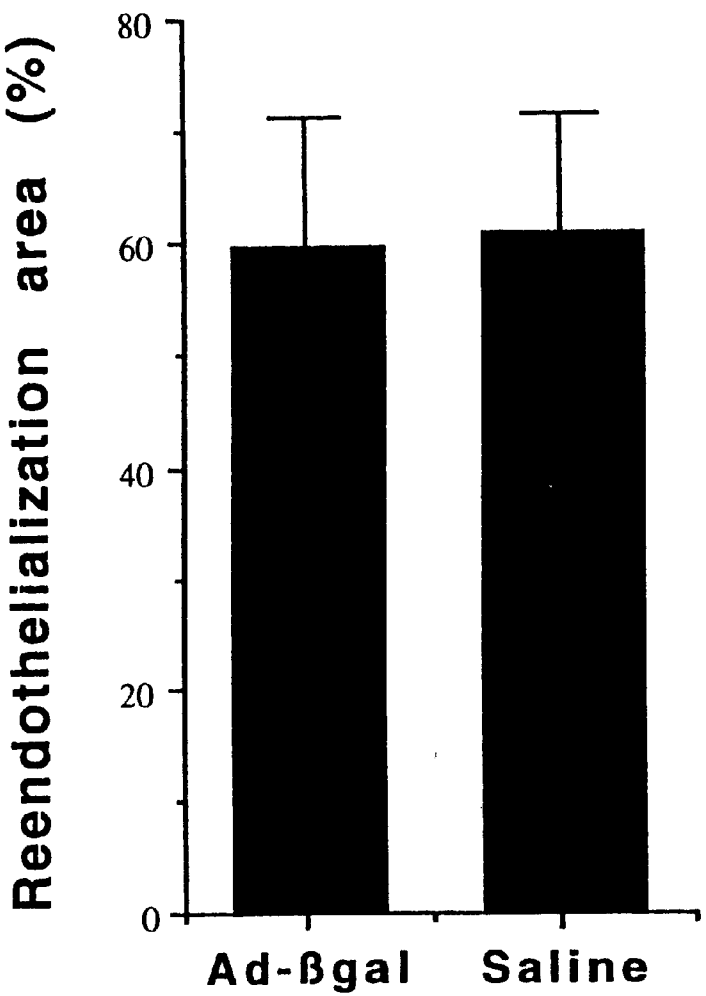
Figure 13A:
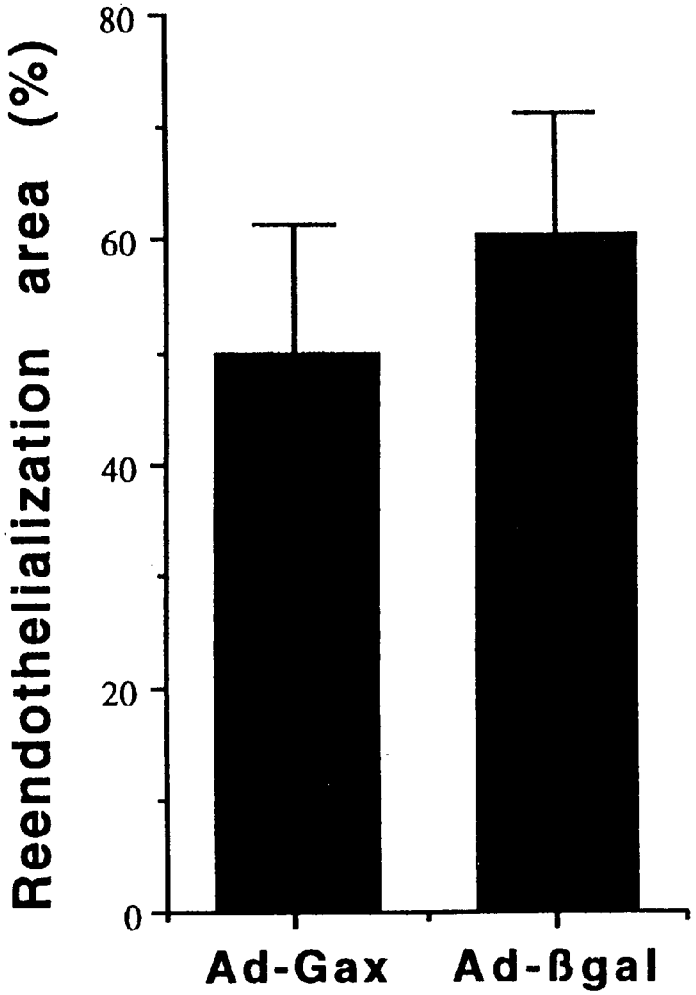

FIGS. 13A and 13B: Summary of extents of reendothelialization at 1 month in the Ad-Gax vs. Ad-β-gal and in the Ad-β-gal vs. saline treated arteries. No significant difference was found in the extents of reendothelialization between arteries infected with Ad-Gax or Ad-βgal (Ad-Gax= 50±11.6% Ad-β-gal=60.6±10.7%). Similarly, no differences were found in the group 2 animals comparing arteries treated with Ad-βgal or saline (Ad-β-gal=59.8±6.9%; saline= 61±5.5).

Figure 14A:
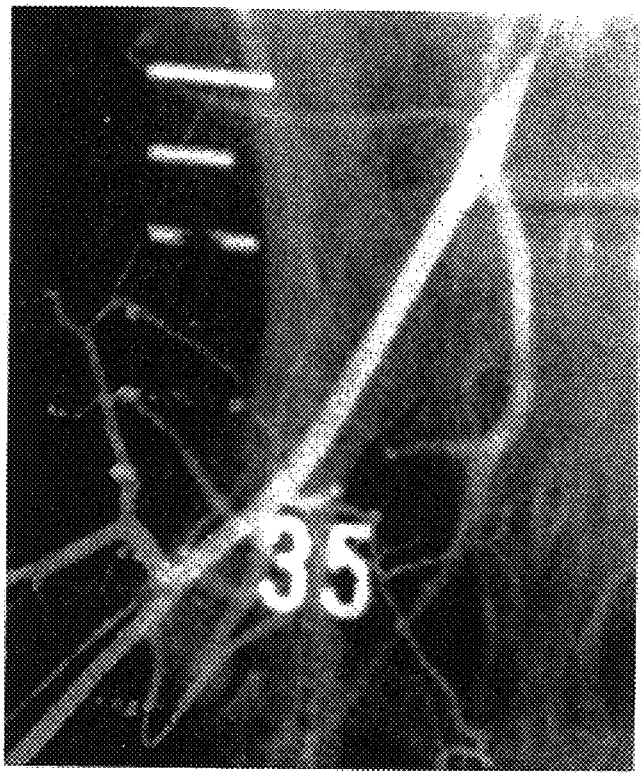
Figure 14B:
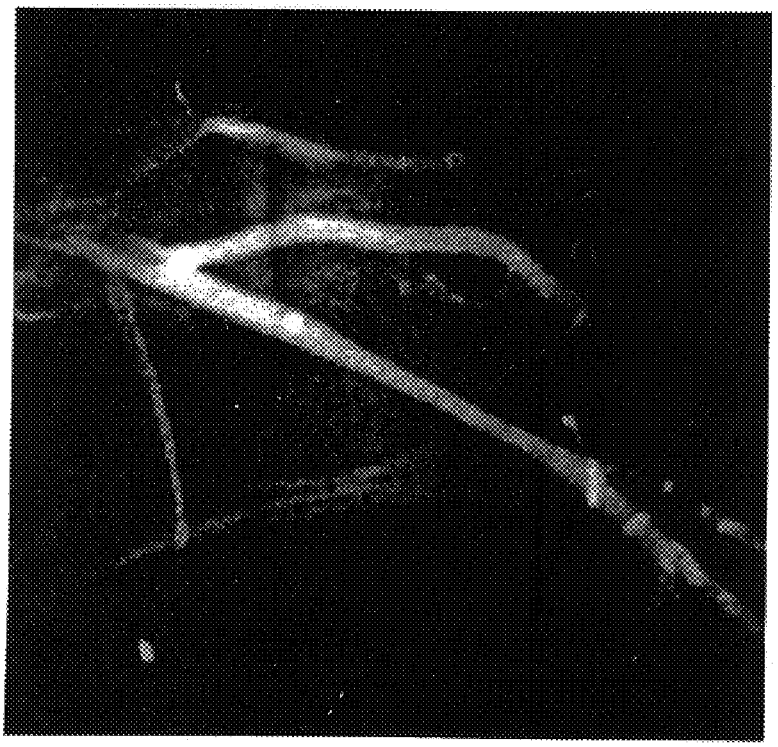

FIGS. 14A and 14B: Ad-Gax infected vessels display larger vessels lumen diameters by angiographic analysis. Representative angiograms obtained after maximal vasodilatation induced by nitroglycerin of the Ad-Gax-(FIG. 14A) and the contralateral Ad-βgal-treated (FIG. 14B) arteries in the same rabbit harvested 28 days after balloon angioplasty and adenoviral infection.

FIGS. 15A–15D: Summary of lumen diameters at 1 month in the Ad-Gax-versus Ad-βgal-treated arteries and in the Ad-βgal-versus the saline-treated arteries obtained after maximal vasodilatation induced by nitroglycerin.

Figure 15B:
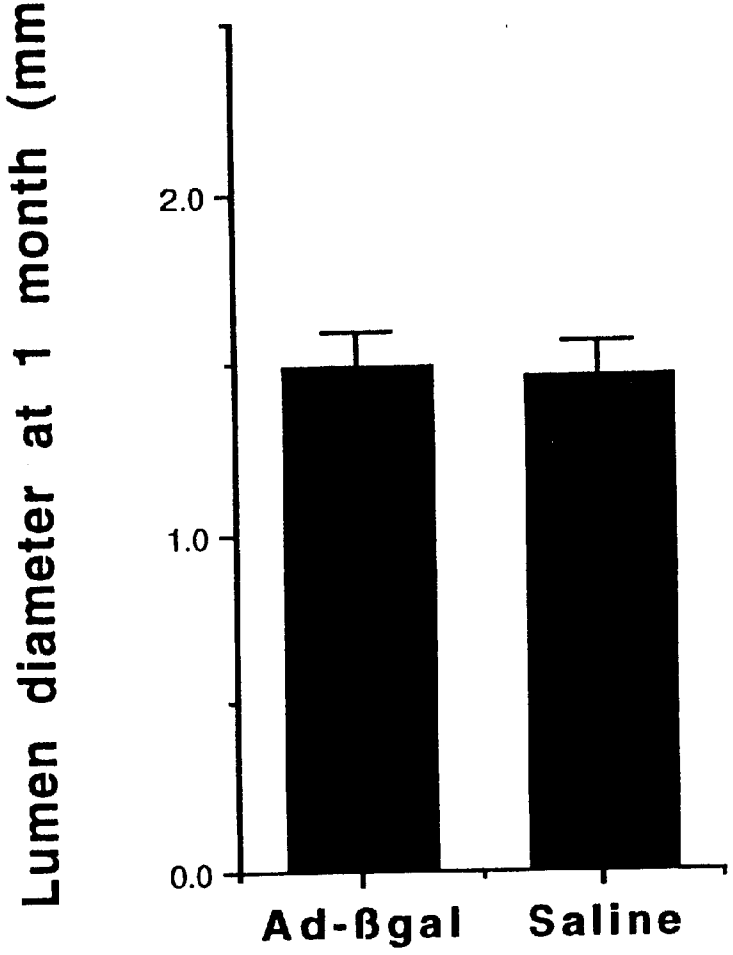
Figure 15A:
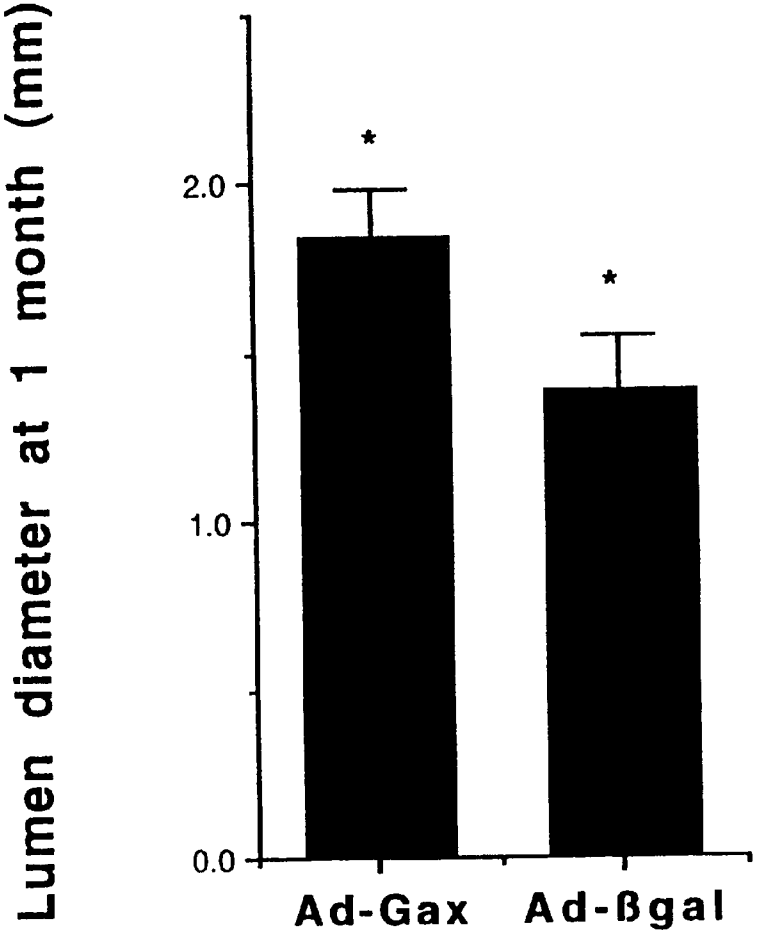

FIGS. 15A and 15B: Lumen diameters after maximal vasodilation induced by nitroglycerine at 28 days post-injury. The Ad-βgal-treated arteries were significantly more narrow than the corresponding Ad-Gax-treated arteries in the group 1 animals ($p=0.006$). No significant differences in luminal narrowing was detected in the second group between vessels treated with Ad-βgal or saline.

Figure 15C:
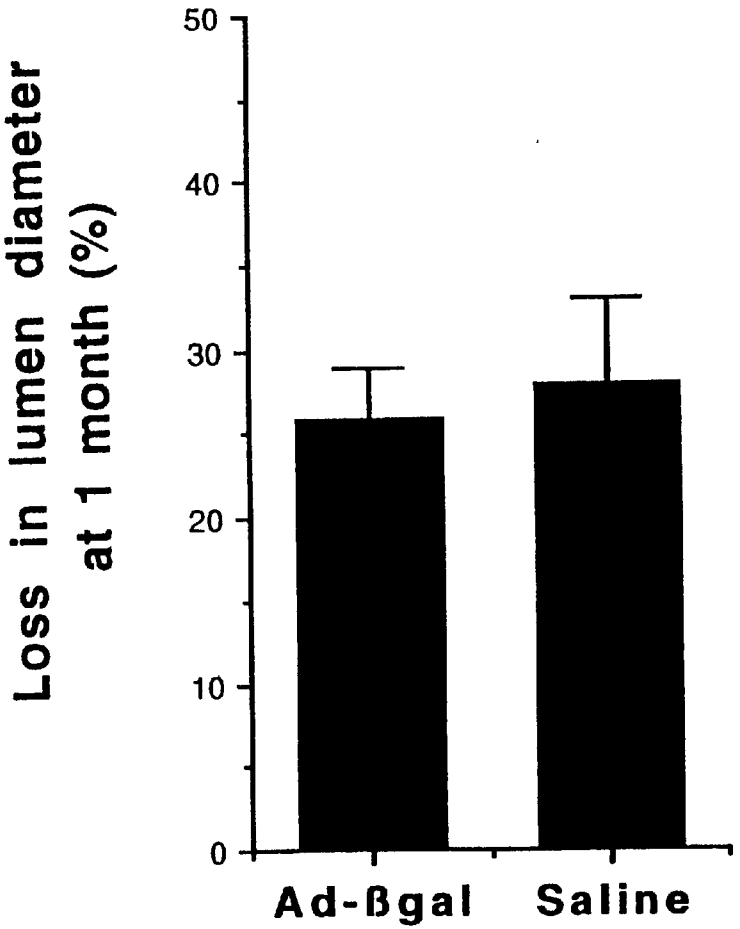
Figure 15D:
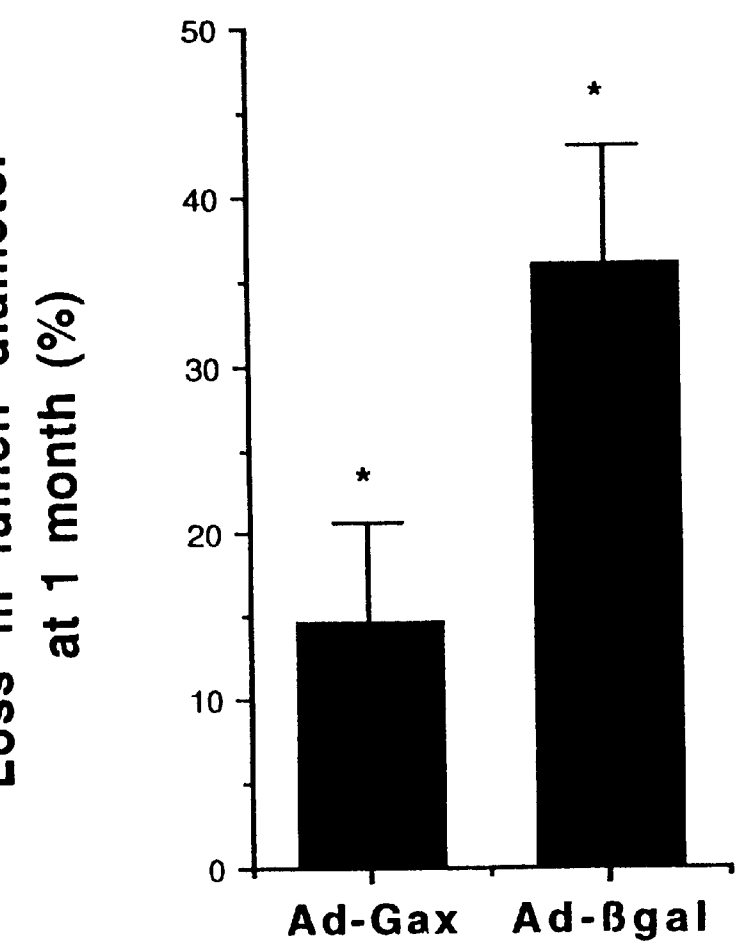

FIGS. 15C and 15D: Results of quantitative angiography expressed as percentage of reduction of lumen diameter relative to reference lumen diameter. A significant difference was found between the vessels infected with Ad-Gax or Ad-β-gal in the first group of animals ($p=0.005$). In the second group no significant difference detected between vessels treated with Ad-β-gal or saline.

FIGS. 16A–16D: Arteries treated bilaterally with Ad-Gax and Ad-gal and saline demonstrated persistent impairment in endothelium-dependent vasomotor response to acetylcholine and serotonin at 28 days post-injury.

Figure 16A:
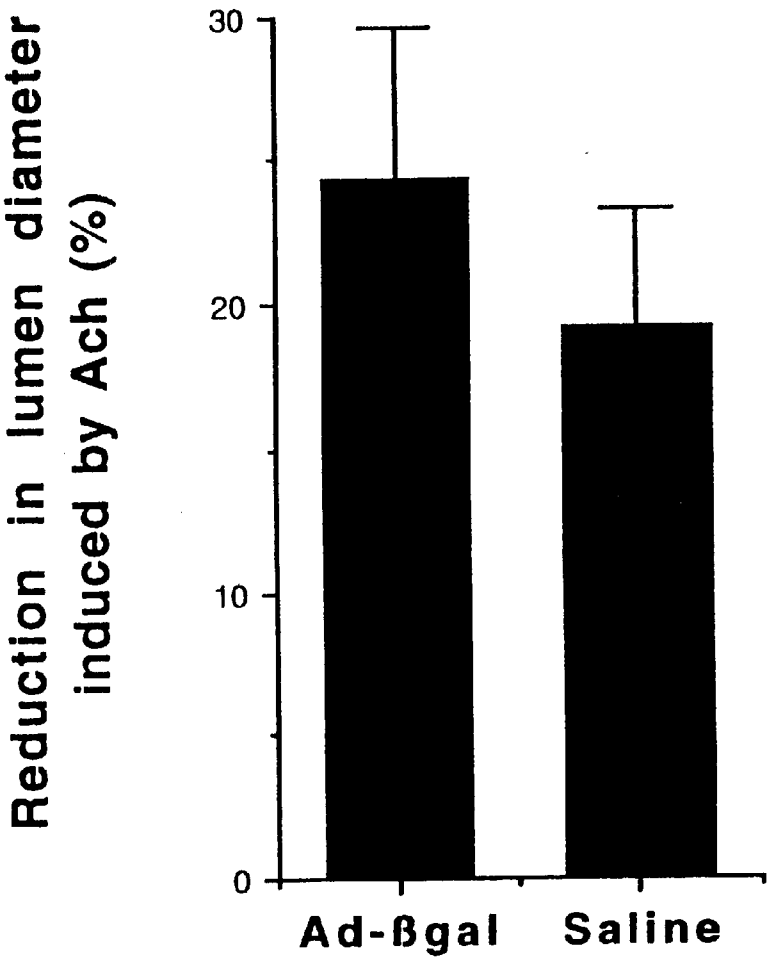
Figure 16B:
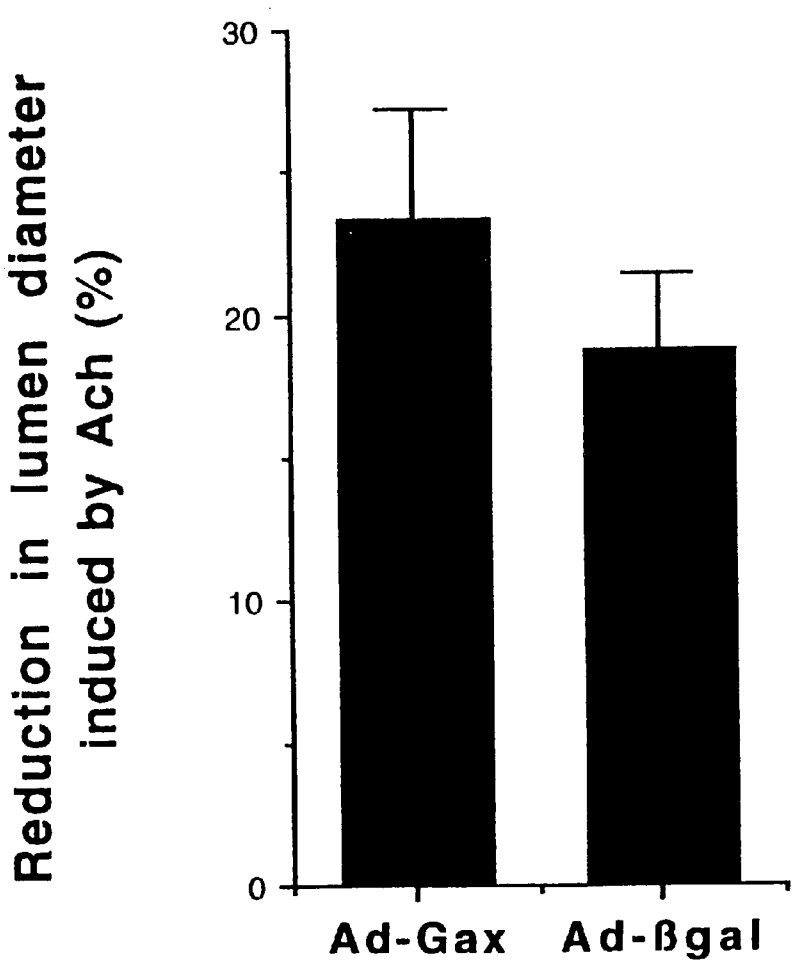
Figure 16C:
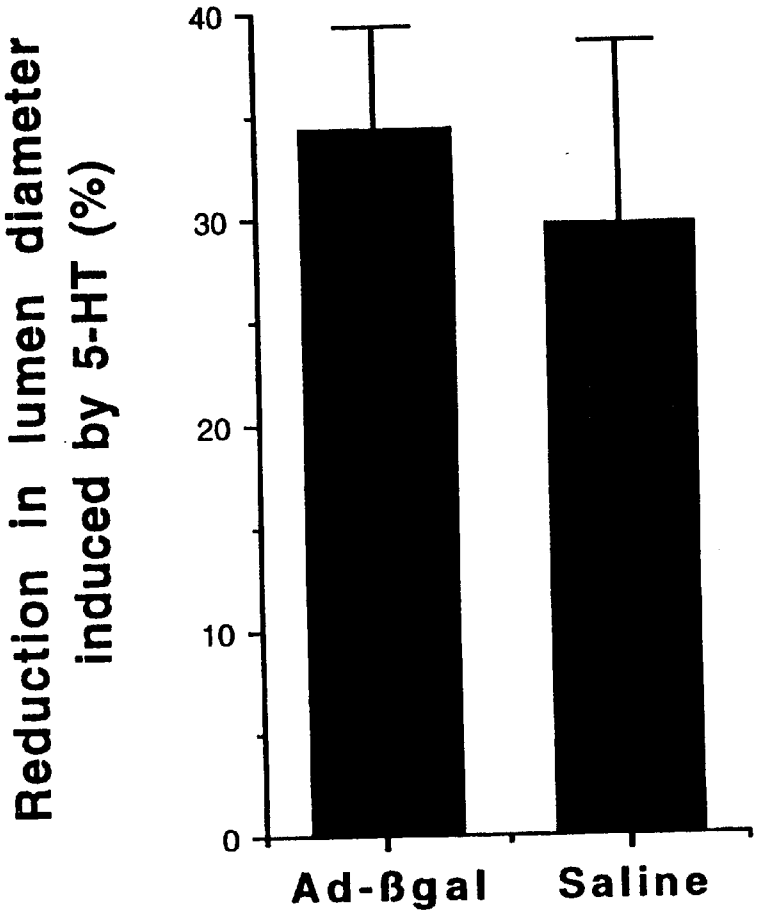
Figure 16D:
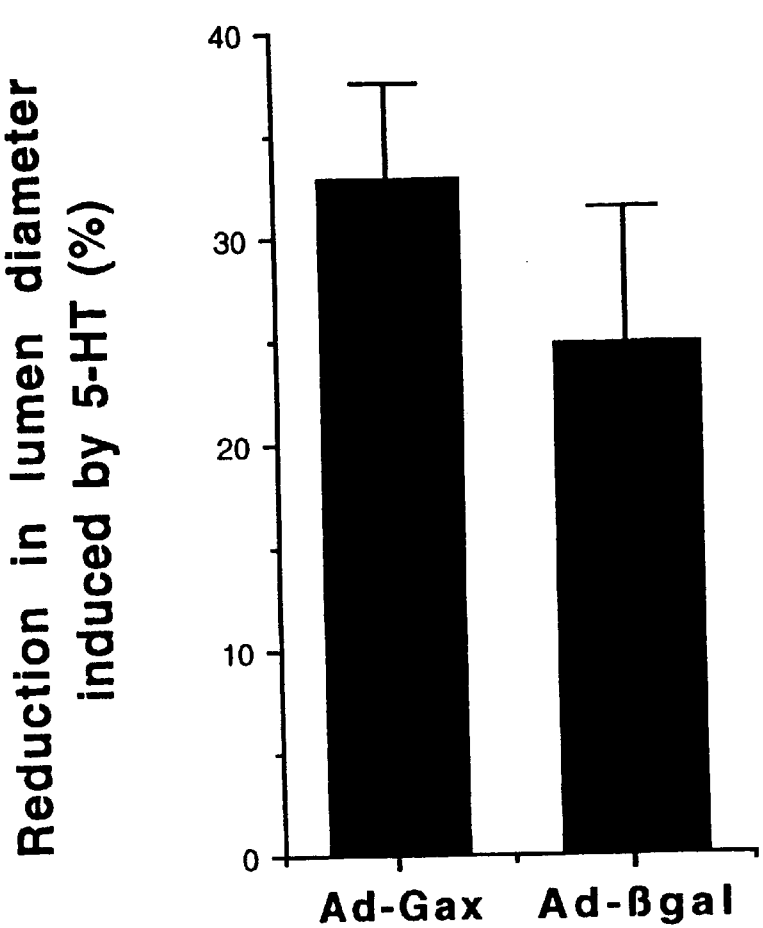

FIGS. 16A and 16D: Bar graphs showing the percentage loss in lumen diameter induced by acetylcholine.

FIGS. 16C and 16D: Bar graphs showing the percentage loss in lumen diameter induced by serotonin. No differences were found between the different sets of vessels in each group.

FIGS. 17A and 17B: Ad-Gax transcript expression in transfected arteries and other tissues 3 days following infection. The results of Gax gene transfer and dissemination was performed using RT-PCR. RNA transcripts specific for recombinant Gax are detectable in all Ad-Gax-treated arteries.

FIG. 17(A): Representative DNA gel demonstrating Ad-Gax expression in the transduced iliac artery (lane 6) and no expression in brain (lane 1), ileum (lane 2), the contralateral saline-treated artery (lane 5), liver (lane 8), heart (lane 9), spleen (lane 10), lung (lane 11), testis (lane 12), kidney (lace 13) or ipsilateral skeletal muscle (lane 14). Also shown are a plasmid (pCGN-Gax) positive control (lane 3) and DNA size markets (lane 7).

FIG. 17(B): Ad-Gax dissemination was detected in 2 of 5 animals. In this representative gel recombinant Gax expression was detected in the Ad-Gax-transduced artery (lane 8), and in spleen (lane 2) and liver (lane 3), but not in brain (lane 5), testis (lane 6), or kidney (lane 7). Also shown are DNA size markers (lane 1) and a plasmid (pCGN-Gax) positive control (lane 4).

DETAILED DESCRIPTION

The invention relates to a replication defective recombinant virus which contains at least one inserted gene encoding all or part of a GAX protein or of a variant of this protein. The invention also relates to the use of such a virus for treating hyperproliferative pathologies.

One advantage of the method according to the invention lies principally in the specificity of the expression of the GAX gene. Thus, in the adult rat, the GAX gene is mainly expressed in the cardiovascular (aorta and heart) system. On We other hand, northern blotting has failed to demonstrate the presence of GAX mRNA in Liver, brain, stomach or skeletal muscle. Post-angioplastic restenesis is a localized hyperproliferative disorder which develops following a non-surgical intervention in the region of the atherosclerotic plaque. The ability to selectively express an antiproliferative gene, such as a GAX gene, according to the invention in VSMC cells provides an effective means for controlling restenosis.

The GAX gene belongs to the family of homeotic genes. These genes encode transcription factors which contain consensus sequences (or homeodomains) which recognize specific regions of the DNA (review : Gehring et al. Cell, 78:211–223, 1994). The homeodomain of the rat GAX protein is contained between amino acids 185 and 245. Interestingly, some of the homeotic genes which have been identified to date are involved in the control of cell differentiation/growth during embryogenesis, thus reinforcing the therapeutic potential of the method according to the invention (review: Lawrence and Morata Cell 78:181–189, 1994; Krumlauf, Cell 78;191–201, 1994).

GAX Gene

The inserted GAX gene can be a fragment of complementary DNA (cDNA) or of genomic DNA (gDNA), or a hybrid construct consisting, for example, of a cDNA into which one or more introns have been inserted. The gene can also consist of synthetic or semi-synthetic sequences. The gene may encode all or part of the GAX protein or a variant of this protein. Within the meaning of the present invention, the term variant denotes any mutant, fragment or peptide which possesses at least one biological property of GAX, as well as any homologue of GAX which is obtained from other species. These fragments and variants may be obtained by any technique known to the person skilled in the art, in particular by genetic and/or chemical and/or enzymic modifications or else by hybridization or by expression cloning, enabling variants to be selected according to their biological activity. The genetic modifications include suppressions, deletions, mutations, etc.

Within the meaning of the invention, the inserted gene is preferably the gene encoding all or part of the rat GAX protein or of its human homologue. It is more preferably a cDNA or a gDNA.

In general, the inserted gene also includes sequences which enable it to be expressed in the infected cell. These sequences can be sequences which are naturally responsible for expressing the said gene, if these sequences are capable of functioning in the infected cell. The sequences can also be sequences of a different origin (responsible for expressing different proteins or even synthetic proteins). In particular, the sequences can be sequences of eukaryotic or viral genes of derived sequences which stimulate or repress transcription of a gene in a specific or non-specific manner and in an inducible or non-inducible manner. As an example, they can be promoter sequences which are derived from the genome of the cell which it is desired to infect or from the genome of a virus, in particular the promoters of the adenoviral ElA and MLP genes, the CMV or the LTR-RSV promoter, etc, Eukaryotic promoters which may also be cited are ubiquitous promoters (HPRT, vimentin, actin, tubulin, etc.), intermediate filament promoters (desmin, neorofilaments, keratin, GFAP, etc.), therapeutic gene promoters (MDR type, CFTR, factor VIII, etc.), tissue-specific promoters (actin promoter in smooth muscle cells), promoters which are preferentially activated in dividing cells, or else promoters which respond to a stimulus (steroid hormone receptor, retinoic acid receptor, etc.). In addition, these expression sequences can be modified by adding activating sequences, regulatory sequences, etc. Otherwise, when the inserted gene does not include any expression sequences, it can be inserted into the genome of the replication defective virus downstream of such a sequence.

Furthermore, the inserted gene may include, upstream of the coding sequence, a signal sequence which directs the synthesized polypeptide into the secretory pathways of the target cell. While this signal sequence can be the natural GAX signal sequence, it can also be any other functional signal sequence (that of the gene for thymidine kinase, for example), or an artificial signal sequence.

Vectors

The viruses according to the present invention are replication defective, that is unable to replicate autonomously in We target cell. In general, the genome of the replication defective viruses which are used within the scope of the present invention lack at least the sequences which are necessary for the replication of the said virus in the infected cell. These regions can either be eliminated (in whole or in part), be rendered non-functional or be substituted by other sequences, in particular by the inserted gene. Preferably, the replication defective virus nevertheless retains the sequences of its genome which are necessary for encapsidating the viral particles.

The virus according to the invention can be derived from an adenovirus, from an adeno-associated virus (AAV) or from a retrovirus. According to one preferred embodiment, the virus is an adenovirus.

Various serotypes of adenovirus exist, whose structure and properties vary somewhat. Of these serotypes, preference is given, within the scope of the present invention, to using type 2 or type 5 human adenoviruses (Ad 2 or Ad 5) or adenoviruses of animal origin (see application WO94/26914). Those adenoviruses of animal origin which can be used within the scope of the present invention and which may be cited are adenoviruses of canine, bovine, murine (example: Mavl, Beard et al., Virology 75 (1990) 81), ovine; porcine, avian or else simian (example: SAV) origin. Preferably, the adenovirus of animal origin is a canine adenovirus, more preferably a CAV2 adenovirus [Manhattan or A26/61 strain (ATCC VR-800), for example]. Preferably, use is made, within the scope of the invention, of adenoviruses of human, canine or mixed origin.

Preferably, the replication defective adenoviruses of the invention comprise the ITRs, an encapsidation sequence and the nucleic acid of interest. Still more preferably, in the genome of the adenoviruses of the invention, at least the E1 region is non-functional. The viral gene under consideration can be rendered non-functional by any technique known to the person skilled in the art, in particular by total removal, substitution, partial deletion or the addition of one or more bases to the genes) under consideration. Such modifications can be achieved in vitro on the isolated DNA) or in situ, for example using the techniques of genetic manipulation or else by treating with mutagenic agents. Other regions may also be modified, in particular the E3 region (WO95/02697), the E2 region (WO4/2938), the E4 region (WO4/28152, WO94/12649 and WO95/02697) and the L5 region (WO5/02697). According to a preferred embodiment, the adenovirus according to the invention contains a deletion in the E1 and E4 regions. According to another preferred embodiment, it contains a deletion in the E1 region into which the E4 region and the sequence encoding GAX are inserted (cf. FR94 13355). In the viruses of the invention, the deletion in the E1 region preferably extends from nucleotides 455 to 3329 in the sequence of the Ad5 adenovirus.

The replication defective recombinant adenoviruses according to the invention can be prepared by any technique known to the person skilled in the art (Levreto et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be mentioned are the human embryonic kidney cell line 293 (Graham et al., J. Gen. Virol. 36 (1977) 59) which contains, in particular, integrated into its genome, the left-hand part of the genome of an Ad5 adenovirus (12%), or cell lines which are able to complement the E1 and E4 functions such as described, in particular, in applications nos. WO94/26914 and WO95/02697.

Subsequently, the adenoviruses which have multiplied are recovered and purified using standard molecular biological techniques, as illustrated in the examples.

The adeno-associated viruses (AAV) are DNA viruses of relatively scaled-down size which integrate, in a stable and site-specific manner, into the genome of the cells which they infect. They are able to infect a wide spectrum of cells without inducing any effects on cellular growth, morphology or differentiation. Furthermore, they do not appear to be involved in human pathologies. The AAV genome has been cloned, sequenced and characterized. It encompasses approximately 4700 bases and contains an inverted terminal repeat (ITR) region of approximately 145 bases at each end, serving as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors delved from the AAVs for transferring genes in vitro and in vivo has been described in the literature (see, in particular, WO 91/18088; WO 93/09239; U.S. Pat. No. 4,797,368, U.S. Pat. No. 5,139,941, EP 488 528). These applications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (TTR) regions, and a plasmid carrying the AAV encapsidation genes (rep and cap genes), into a cell line which is infected with a human helper virus (for example an adenovirus). The AAV recombinants which are produced are then purified by standard techniques. The invention also relates, therefore, to as AAV-derived recombinant virus whose genome encompasses a sequence encoding GAX flanked by the AAV ITRs. The invention also relates to a plasmid encompassing a sequence encoding GAX flanked by two ITRs from an AAV Such a plasmid can be used as it is for transferring the GAX sequence, with the plasmid, where appropriate, being incorporated into a liposomal vector (pseudo-virus).

The construction of recombinant retroviral vectors has been widely described in the literature: see, in particular, EP 453242, EP178220, Bernstein et al. Genet. Eng. 7 (1985) 235; McCormick, BioTechnology 3 (1985) 689, etc. In particular, the retroviruses are integrating viruses which infect dividing cells. The retrovirus genome mainly encompasses two LTRs, an encapsidation sequence and three coding regions (gag, pot and envy. In the retrovirus-derived recombinant vectors, the gag, pot and env genes are generally deleted, in whole or in part, and replaced with a heterologous nucleic acid sequence of interest. These vectors can be constructed from different types of retrovirus such as, in particular, MoMuLV ("murine Moloney leukaemia virus"; also designated MoMLV), MSV ("marine Moloney sarcoma virus"), HaSV ("Harvey sarcoma virus"); SNV ("spleen necrosis virus"); RSV ("Rous sarcoma virus") or else Friend virus.

In general, in order to construct recombinant retroviruses containing a sequence encoding GAX according to the invention, a plasmid is constructed which contains, in particular, the LTRs, the encapsidation sequence and the said coding sequence and is then used to transfect what is termed an encapsidation cell line, which cell line is able to supply in traps the retroviral functions which are deficient in the plasmid. In general, the encapsidation cell lines are thus able to express the gag, pot and env genes. Such encapsidation cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviruses can contain modifications within the LTRs for suppressing transcriptional activity as well as extensive encapsidation sequences which include a part of the gag gene (Bender et al., J. Virol. 61(1987) 1639). The recombinant retroviruses which have been produced are then purified by means of standard techniques.

It is very particularly advantageous to use a replication defective recombinant adenovirus for treating restenosis. Thus, adenoviruses possess a high capacity for infecting proliferating vascular smooth-muscle cells. This allows relatively low quantities of the active principle (recombinant adenovirus) to be used and also results in effective and very rapid action on the sites to be treated. The adenoviruses of the invention are also able to express the introduced GAX gene at high levels, thereby conferring on them a very efficient therapeutic action. Furthermore, due to their episomal nature, the adenoviruses of the invention only persist for a limited time in the proliferative cells and therefore have a transitory effect which is perfectly suited to the desired therapeutic effect.

Pharmaceutical Compositions and Devices

The present invention also includes within its scope pharmaceutical compositions comprising one or more replication defective recombinant viruses, as previously described, dispersed in a physiologically acceptable medium, which is preferably buffered to physiologically normal pH. Such compositions can be formulated for administration by topical, oral, parenteral, intranasal, subcutaneous, intraocular, routes. The composition may be administered parenterally in dosage unit formulations containing standard, well known nontoxic physiologically acceptable carriers, adjuvants and vehicles as desired. Parenteral administration is meant to include intravenous injection, intramuscular injection, intraarterial injection or infusion techniques.

The preferred parenteral compositions according to the invention comprise excipients which are pharmaceutically acceptable for an injectable formulation, in particular for injection within the vasculature. Injectable preparations are further preferably sterile, and may be aqueous or oleaginous suspension formulated using suitable dispersing or wetting agents and suspending agents. The preferred sterile injectable preparations can also be a solution or suspension in a nontoxic parenterally acceptable solvent or diluent. Excipients can, in particular, be sterile water, Ringer's solution, and isotonic saline solutions (monosodium or disodium phosphate, sodium, potassium, calcium or magnesium chloride, or mixtures of such salts). 1,3-butanediol and sterile fixed oils are conveniently employed as solvents or suspending media. Any bland fixed oil can be employed including synthetic mono- or di-glycerides. Fatty acids such as oleic acid also find use in the preparation of injectables. Injectable solutions may be prepared by combining sterilized water or physiological saline with a dry, e.g. lyophilized, virus composition.

More preferably, the composition will be formulated in a manner which resists rapid clearance from the vascular (arterial or venous) wall by convection and/or diffusion, thereby increasing the residence time of the viral particles at the desired site of action. A periadventitial depot comprising the vector of the present invention may be used for sustained release. A preferred depot useful in administering the vector of the invention may be a copolymer matrix, such as ethylene-vinyl acetate, or a polyvinyl alcohol gel surrounded by a Silastic shell. Alternatively, the composition may be delivered locally from a silicone polymer implanted in the adventitia.

An alternative approach for minimizing drug washout during percutaneous, transvascular delivery comprises the use of nondiffusible, drug-eluting microparticles. The microparticles may be comprised of a variety of synthetic polymers, such as polylactide for example, or natural substances, including proteins or polysaccharides. Such microparticles enable strategic manipulation of variables including total dose of drug and kinetics of its release. Microparticles can be injected efficiently into the arterial or venous wall through a porous balloon catheter or a balloon over stmt, and are retained in the vascular wall and the periadventitial tissue for at least about two weeks. Formulations and methodologies for local, intravascular site-specific delivery of therapeutic agents are discussed in Reissen et al. (*J. Am. Coll. Carttiol.* 1994; 23:1234–1244), the entire contents of which are hereby incorporated by reference.

The composition medium can also be a hydrogel which is prepared from any biocompatible or non-cytotoxic (homo or hereto) polymer, such as a hydrophilic polyacrylic acid polymer that can act as a drug absorbing sponge. Such polymers have been described, for example, in application WO93/08845, the entire contents of which are hereby incorporated by reference. Certain of them, such as, in particular, those obtained from ethylene and/or propylene oxide are commercially available.

In their use for treating pathologies which are linked to hyperproliferative disorders, the replication defective recombinant viruses according to the invention can be administered in different ways. Preferably, for the treatment of restenosis, the viruses of the invention are administered directly to the blood vessel wall by means of an angioplasty balloon which is coated with a hydrophilic film (for example a hydrogel) which is saturated with the virus, or by means of any other catheter containing an infusion chamber for the viral composition, which can thus be applied in a precise manner to the site to be treated and allow the viruses to be liberated locally and efficiently at the location of the cells to be treated. This method of administration advantageously makes it possible to infect a high percentage (up to 9.6%) of the cells of the tunica media, which constitute the preferred target for treating restenosis, whereas the standard methods of administration (intravenous injection, for example) do not enable these cells to be infected to this degree.

The treatment method of the invention preferably consists in introducing a composition comprising a hydrogel saturated with recombinant viruses at the site to be treated. The hydrogel can be deposited directly onto the surface of the tissue to be treated, for example during a surgical intervention. Advantageously, the hydrogel is introduced at the desired intravascular site by coating a catheter, for example a balloon catheter, and delivery to the vascular wall, preferably at the time of angioplasty. In a particularly advantageous manner, the saturated hydrogel is introduced at the site to be treated by means of a balloon catheter. The balloon may be chaperoned by a protective sheath as the catheter is advanced toward the target vessel, in order to minimize drug washoff after the catheter is introduced into the bloodstream.

Another embodiment of the invention provides for the recombinant viruses to be administered by means of perfusion balloons. These perfusion balloons, which make it possible to maintain a blood flow and thus to decrease the risks of ischaemia of the myocardium, on inflation of the balloon, also enable a medicinal product to be delivered locally at normal pressure for a relatively long time, more than twenty minutes, which may be necessary for an optimal infection. Alternatively, a channelled balloon catheter ("channelled balloon angioplasty catheter", Mansfield Medical, Boston Scientific Corp., Watertown, Mass.) may be used. The latter consists of a conventional balloon covered with a layer of 24 perforated channels which are perfused via an independent lumen through an additional infusion orifice. Various types of balloon catheters, such as double balloon, porous balloon, microporous balloon, channel balloon, balloon over stent and hydrogel catheter all of which may be used to practice the invention, are disclosed in Reissen et al. (1994).

It is especially advantageous to use a perfusion balloon catheter. In this case, the advantages of both keeping the balloon inflated for a longer period of time by retaining the properties of facilitated sliding and of site-specificity of the hydrogel, are gained simultaneously. In this case, an optimal efficacy of infection is obtained.

Another preferred embodiment of the present invention relates to a pharmaceutical composition comprising a replication defective recombinant virus and poloxamer. More specifically, the invention relates to a composition comprising a replication defective recombinant virus comprising a GAX gene and poloxamer. Poloxamer 407 is a non-toxic, biocompatible polyol, is commercially available (BASF, Parsippany, N.J.) and is most preferred.

A poloxamer impregnated with (recombinant viruses may be deposited directly on the surface of the tissue to be treated, for example during a surgical intervention. Poloxamer possesses essentially the same advantages as hydrogel while having a lower viscosity.

It is especially advantageous to use a channel balloon catheter and poloxamer. In this case, the advantages of both keeping the balloon inflated for a longer period of time, while retaining the properties of facilitated sliding, and of site-specificity of the poloxamer, are gained simultaneously, thereby optimizing efficacy of infection.

The doses of virus which are used for the injection can be adjusted according to different parameters, in particular according to the mode of administration employed, desired duration of treatment and condition of the patient. The dose may be determined by a physician or qualified medical professional. In each particular case, the doses are determined in accordance with factors distinctive to the patient, such as age, weight, general state of health and other characteristics which can influence the efficiency of the compound according to the invention.

Generally, the recombinant viruses according to the invention are formulated and administered in the form of doses of between about $10^4$ and about $10^{14}$ pfu. In the case of AAVs and adenoviruses, doses of from about $10^6$ to about $10^{10}$ pfu can also be used. The term pfu ("plaque-forming unit") corresponds to the infective power of a suspension of virions and is determined by infecting an appropriate cell culture and measuring, generally after 48 hours, the number of plaques of infected cells. The techniques for determining the pfu titre of a viral solution are well documented in the literature.

The present invention offers a novel and very efficient means for treating or preventing pathologies linked to hyperproliferative disorders such as restenosis.

Furthermore, this treatment can relate just as well to humans as to any animals such as sheep, cattle, domestic animals (dogs, cats), homes, and fish.

The present invention is more completely described using the examples which follow and which should be considered as being illustrative and not limiting.

GENERAL MOLECULAR BIOLOGICAL TECHNIQUES

The standard methods employed in molecular biology, such as preparative extractions of plasmid DNA, centrifugation of plasmid DNA in a caesium chloride gradient, electrophoresis on agarose or acrylamide gels, purification of DNA fragments by electroelution, extraction of proteins with phenol or with phenol/chloroform precipitation of DNA in a saline medium using ethanol or using isopropanol; transformation into *Eschericia coli*, etc. . . . , are well known to the person skilled in the art and are amply described in the literature [Maniatis T et al., "Molecular Cloning, A Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type, and phages of the M13 series were obtained commercially (Bethesda Research Laboratories).

For ligations, the DNA fragments can be separated according to their size by electrophoresis in agarose or acrylamide gels, extracted with phenol or with a phenol/chloroform mixture, precipitated with ethanol and then incubated in the presence of T4 DNA ligase (Biolabs) in accordance with the supplier's recommendations.

5' protruding ends can be filled in using the Klenow fragment of *E. coli* DNA polymerase I (Biolabs) in accordance with the supplier's specifications. 3' protruding ends are destroyed in the presence of T4 DNA polymerase (Biolabs), which is used in accordance with the manufacturer's recommendations. 5' protruding ends are destroyed by careful treatment with S1 nuclease.

In-vitro site-directed mutagenesis using synthetic oligodeoxynucleotides can be carried out in accordance with the method developed by Taylor et al. [Nucleic Acids Res. 13 (1985) 8744–8764] employing the kit distributed by Amersham.

Enzymic amplification of DNA fragments by means of the technique termed PCR [polymerise-catalyzed chain reaction, Saiki R. K. et al., Science 230 (1985) 1350–1354; Mullis K. B. and Faloona F. A., Meth. Enzym. 155 (1987) 335–350] can be effected using a DNA thermal cycler (Perkin Elmer Cetus) in accordance with the manufacturer's specifications.

Nucleotide sequences can be ascertained by means of the method developed by Singer et al. [Proc. Natl. Acid. Sci. USA, 74, (1977) 5463–5467] using the kit distributed by Amersham.

EXAMPLE 1 construction of the vector pXL-CMV-GAX$^{HA}$, carrying the gene encoding the rat GAX protein under the control of the CMV promoter This example describes the construction of a vector which contains the cDNA encoding the GAX protein (species: rat) and adenoviral sequences which enable recombination to take place. The epitope of influenza virus haemagglutinin (epitope HA1), encompassing 18 amino acids, is added to the N-terminal end of the GAX protein (Field et al., Mol.Cell.Biol. 8:2159–2165, 1988). Adding the epitope in this way enables GAX expression to be followed, in particular by immunofluorescence techniques, using antibodies which are directed against the HA1), epitope. In addition to its sensitivity, this method at the same time makes it possible to eliminate, both in vitro and in vivo, the background noise corresponding to the expression of endogenous GAX proteins.

1.1. Construction of plasmid pCO1

A—Construction of plasmid pCE

The EcoRI/Xbal fragment corresponding to the left-hand end of the Ad5 adenovirus genome was first of all cloned between the EcoRI and Xba sites of the vector pCB19H. This generates plasmid pCA: Plasmid pCA was then cut with HinfI and its 5' protruding ends were filled in using the Klenow fragment of *E.coli* DNA polymerase I; it was then cut with EcoRI. The fragment of plasmid pCA which was thus generated, and which contains the left-hand end of the Ad5 adenovirus genome, was then cloned between the EcoRI and SmaI sites of the vector plC20H (Marsh et al., Gene 32 (1984) 481). This generates plasmid pCB. Plasmid pCB was then cut with EcoRI and its 5' protruding ends were filled in using the Klenow fragment of *E.coli* DNA polymerase I; it was then cut with BamHI. The fragment of plasmid pCB which was thus generated, and which contains the left-hand end of the Ad5 adenovirus genome, was then cloned between the NruI and BglII sites of vector plC20H. This generates plasmid pCE an advantageous characteristic of which is that it possesses the first 382 base pairs of the Ad5 adenovirus followed by a multiple coning site.

B—Construction of plasmid pCD'

The Sau3A (3346)/SstI (3645) and SstI (3645)/NarI (5519) fragments from the genome of the Ad5 adenovirus were first of all ligated together and cloned between the ClaI and BamHI sites of vector plC20H, thereby generating plasmid pPY53. The SalI/TaqI fragment from plasmid pPY53 (prepared from a dam- background), containing the part of the Ad5 adenovitus genome between the Sau3A (3346) and TagI (5207) sites, was then cloned between the SalI and ClaI sites of vector plC20H, thereby generating plasmid pCA'. The TagI (5207)/NarI (5519) fragment of the Ad5 adenovirus genome, prepared from a dam- background, and the SalI-TaqI fragment from plasmid pCA' were then ligated together and cloned between the SalI and NarI sites of vector plC20H. This generates plasmid pCC'. The NarI (5519)/NruI (6316) fragment of the Ad5 adenovirus genome, prepared from a dam- background, and the SalI/NarI fragment of plasmid pCC' were then ligated together and cloned between the SalI and NruI sites of vector plC20R. This generates plasmid pCC'.

C—Construction of plasmid pC01

Partially digesting plasmid pCD' with XhoI and then completely digesting it with SalI generates a restriction fragment which contains the Ad5 adenovirus sequence from the Sau3A (3446) site to the NruI (6316) site. This fragment was cloned into the SalI site of plasmid pCE. This generates plasmid pC01 (FIG. 1), which contains the left-hand part of the Ad5 adenovirus up to the HinfI (382) site, a multiple cloning site and the Sau3A (3446)/NruI (6316) fragment of the Ad5 adenovirus.

Figure 2:
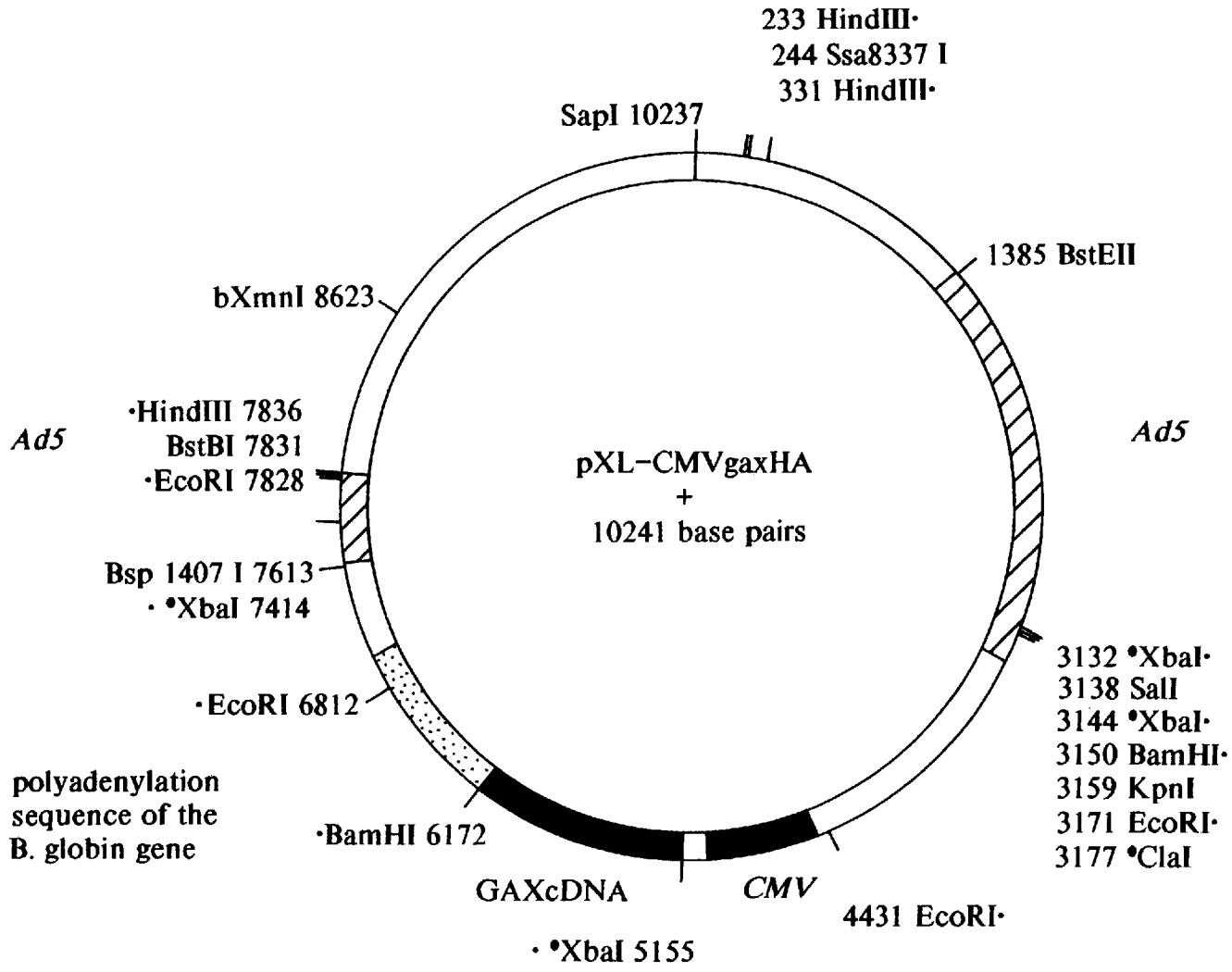
FIG. 2: Depiction of the plasmid pXL-CMV-GAX$^{HA}$.

1.2. Construction of vector pXL-CMV-GAX$^{HA}$ (cf. FIG. 2)

The GAX cDNA was cloned between the XbaI and BamHI sites of vector pCGN (Tanaka and Herr, Cell 60:375–386,1990). The resulting vector, pGCN-GAX, contains the early promoter and enhancer sequence of cytomegalovirus (CMV) (−522, +72; Boshart et al, Cell, 41:521–530, 1985), the leader sequence of herpes simplex virus thymidine kinase, including the AUG initiation colon, as well as the first three amino acids (+55, +104; Rusconi and Yamamoto, EMBO J., 6:1309–1315,1987), the sequence encoding the HA1), epitope [Y P Y D V P D Y A S L G G P (SEQ ID No. 1)], the rat GAX cDNA and, finally, the polyadenylation sequence of the rabbit β-globin gene (Pabo et al, Cell, 35:44553, 1983).

Vector pCGN-GAX was then cut with XmnI and SfiI and the resulting fragment, containing the promoter, the cDNA and the polyadenylation sequence, was introduced, after first having been treated with Klenow, into the EcoRV site of the shuttle vector pC01, which contained the adenoviral sequences required for recombination. The plasmid which was obtained was designated pXL-CMV-GAX$^{HA}$ (cf. FIG. 2).

EXAMPLE 2 demonstration of the proliferation-inhibiting properties of plasmid pXL-CMV-GAX-HA This example describes the operative procedures which can be used to demonstrate, in vitro and at one and the same time, the quality of the homologous recombination vectors (cf. Example 1) as regards expression (detection of the GAX protein and the HA epitope) and as regards activity (effect on cell proliferation).

The vascular smooth muscle cells (VSMC's) are cultured by enzymically digesting NZW rabbit aorta using a method adapted from Chamley et al. (Cell Tissue Res. 177:503–522 (1977) Briefly, once having been removed, the rabbit aorta is incubated at 37° C. for 45 minutes in the presence of collagenase (collagenase II, Cooper Biomedical). A second digestion is then carried out for approximately two hours in the presence of collagenase and elastase (Biosys), thereby giving rise to a cell suspension. The cells are maintained in the presence of 20% foetal calf serum and used for all the tests (cf. below) prior to the tenth passage. In all these experiments, the smooth muscle cells are characterized by immunolabelling by means of anti-αSM actin antibody (F-3777, Sigma).

In order to verify the quality of the expression vectors (cf. Example 1), the presence and the location of the GAX protein are monitored by immunofluorescence for each construct. In order to do this, the smooth muscle cells or the 3T3 cells are transfected with plasmids pXL-CMV-GAX$^{HA}$ and pCGNGAX in the presence of a DOSPA/DOPE mixture (Lipofectamine, Gibco BRL). The cells are incubated in the presence of the DNA/liposome complex in a culture medium lacking foetal calf serum for 4 to 8 hours (optimal duration: 8 hours for the SMCs). After incubating for 24 hours in the presence of foetal calf serum, the cells are cultured on a microscope slide (Titertek), with a view to immunofluorescence, for a further 24 hours. The cells are then fixed in the presence of 4% paraformaldehyde and subsequently permeabilized by adding 0.1% triton. After saturating the cells in the presence of bovine serum albumin (BSA, Sigma), anti-HA antibody (12CA5, Boehringer Mannheim) and then fluorescein-conjugated antibody are added in succession.

Figure 3A:
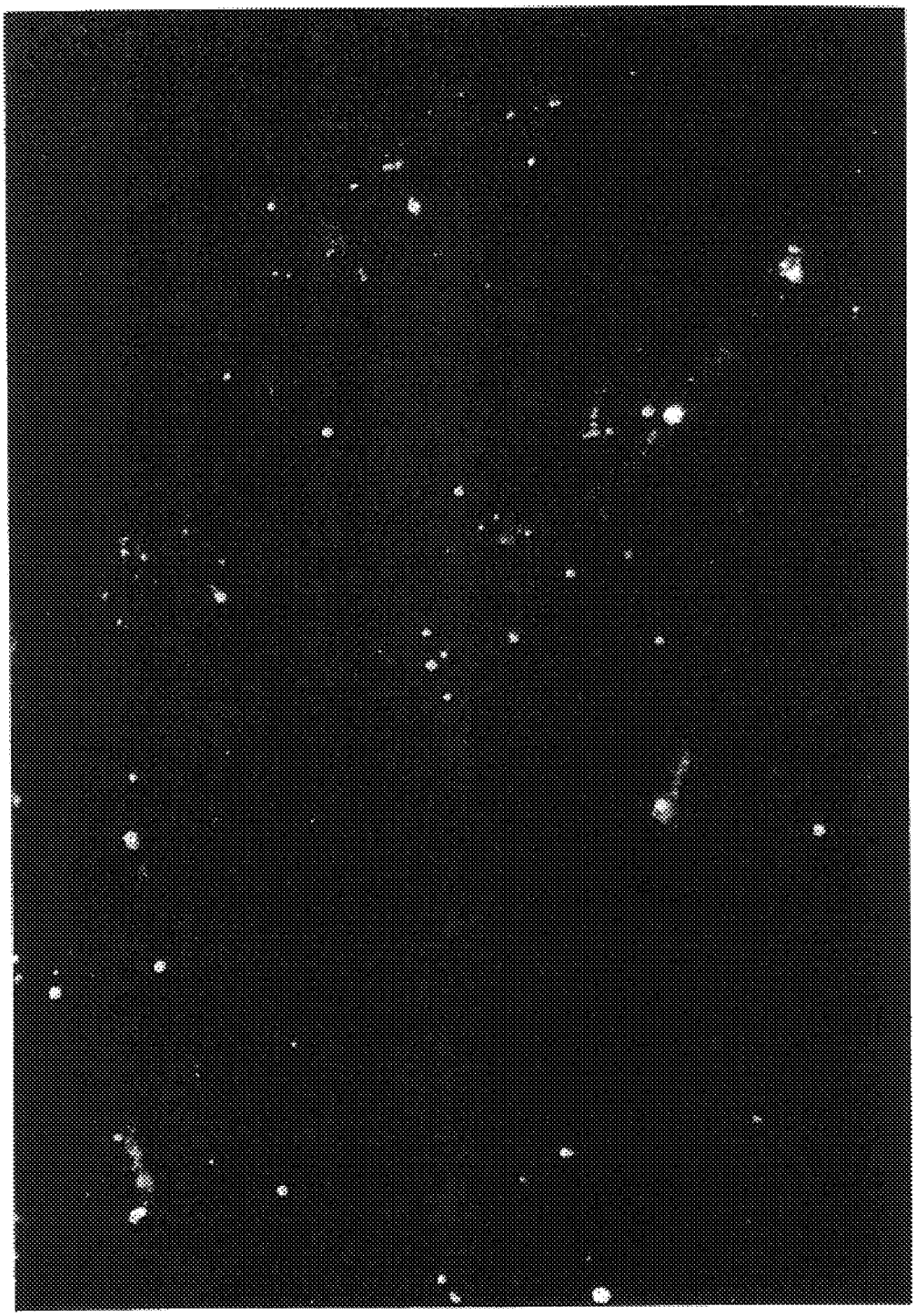
FIGS. 3A and 3B: Nuclear location of the GAX-HA protein in the VSMCs transfected with pXL-CMV-GAX$^{HA}$.
Figure 3B:
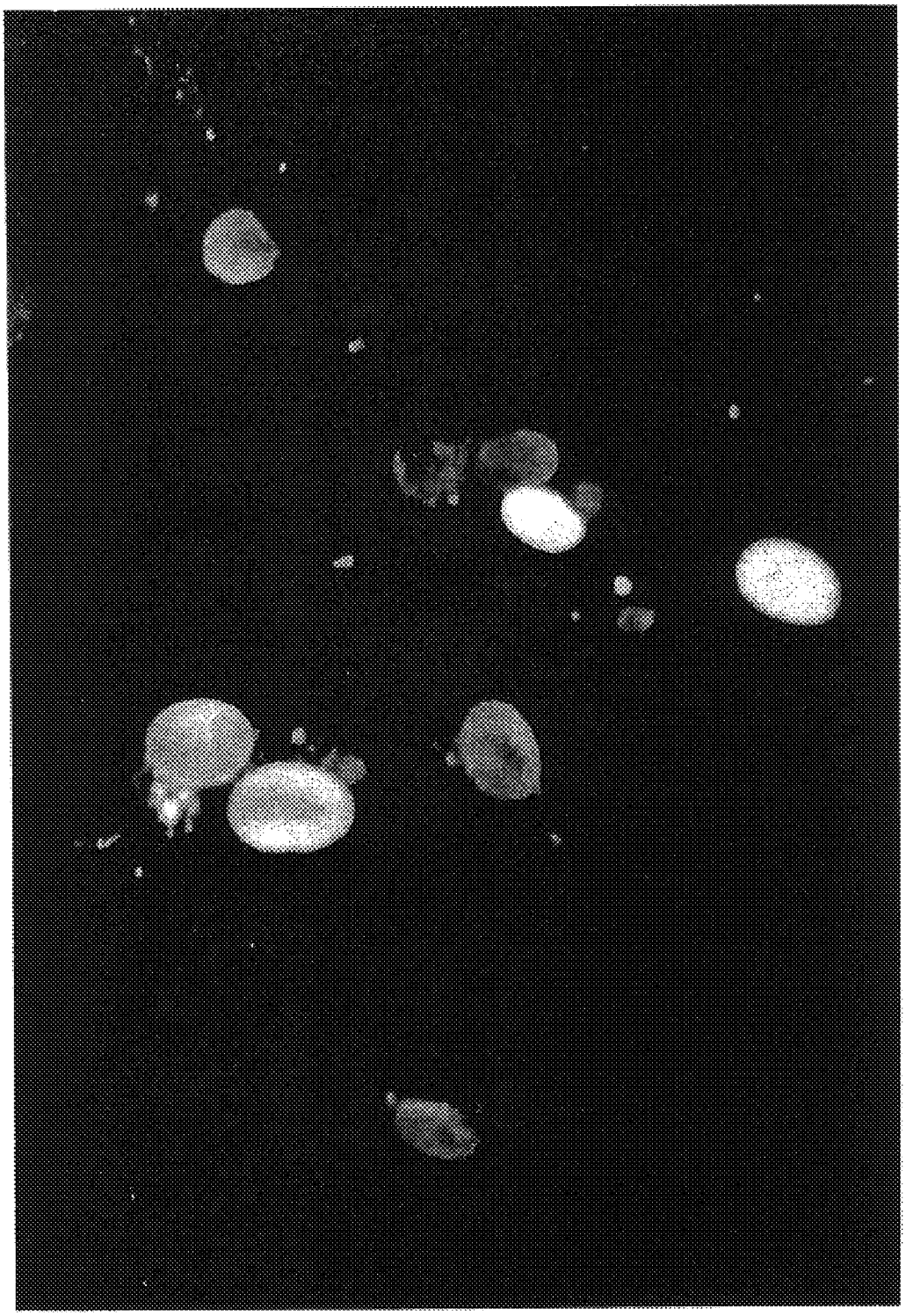

Immunofluorescence experiments carried out simultaneously on NIH3T3 cells and on a primary culture of rabbit VSMCs demonstrate that both plasmid pCGNGAX and the "shuttle" plasmid pXL-CMV-GAX$^{HA}$ do indeed encode a protein which is located in the nucleus (cf. FIG. 3A: control plasmid; 3B: plasmid pXL-CMV-GAX$^{HA}$). Furthermore, following extraction of the nuclear proteins from cells transfected with pXL-CMV-GAX$^{HA}$, we were able to demonstrate, by means of western blotting, a protein which is detected with antibodies directed against the HA epitope.

The effect of the above vectors on cell proliferation was then ascertained. In order to do this, an indirect method was used which is based on measuring colony formation. Briefly, NIH3T3 mouse embryonic cells were employed to carry out colony-formation tests using a method which was adapted from Schweighoffer et al. (Mol.Cell.Biol. 1993, 13:39–43). Briefly, the cells are cotransfected with a plasmid carrying the gene for resistance to neomycin and with an excess of the vector of interest (PCGNGAX or pXL-CMV-GAX$^{HA}$). After a period of selection in G418, the colonies are stained with a solution of carbol fuchsia (Diagnostics, Merck) and counted. The results of a representative experiment, which are given in Table 1, demonstrate a decrease in the number of colonies in the case of cells transferred with pCGNGAX.

TABLE 1

| 3T3 cell transfection conditions | Number of colenies following selection in G41K |
|---|---|
| pCGN (5 μg) + pS$^V$2neo (1 μg) (§) | 183 ± 28 (+) |
| pCGNGAX (5 μg) + pS$^V$2neo (1 μg) | 93 ± 11 |

(§) PCGN control vector; absence of GAX insert
(+) $p < 0.02$

EXAMPLE 3

Construction of the recombinant adenovirus Ad-CMVGAX

Vector pXL-CMV-GAX$^{HA}$, which was prepared in Example 1, was subsequently linearized and cotransfected for recombination, with a deficient adenoviral vector into helper cells (cell line 293) which supplied in traps the functions encoded by the adenovirus E1 E1A and E1B) regions.

The adenovirus Ad-CMVGAX was obtained by means of in-vivo homologous recombination between the adenovirus Ad.RSVβgal (Stratford Perricaudet et al., J. Clip. Invest 90 (1992) 626) and vector pXL-CMV-GAX$^{HA}$ in accordance with the following protocol: vector pXL-CMV-GAX$^{HA}$, linearized with the enzyme XmnI, and adenovirus Ad.RSVβgal linearized with ClaI, were cotransfected into cell line 293 in the presence of calcium phosphate in order to enable homologous recombination to take place. The recombinant adenoviruses which were generated in this way were selected by plaque purification. Following isolation, the recombinant adenovirus is amplified in cell line 293, resulting in a culture supernatant which contains the non-purified recombinant replication defective adenovirus having a titre of approximately $10^{10}$ pfu/ml.

The viral particles are purified by centrifugation on a caesium chloride gradient in accordance with the known techniques (see, in particular, Graham et al., Virology 52 (1973) 456). The adenovirus Ad-CMVGAX is stored at −80° C. in 20% glycerol.

EXAMPLE 4

Demonstration of the proliferation-inhibiting properties of adenovirus Ad-CMVGAX This example describes the experimental procedures which can be used to demonstrate, at one and the same time, the quality of the recombinant adenovirus in terms of GAX protein production and in terms of biological activity (effect on cell proliferation).

The rabbit aorta VSMCs are incubated in the presence of adenovirus Ad-CMVGAX$^{HA}$ and a control adenovirus (ad-RSVβGal: recombinant adenovirus expressing β-galactosidase under the control of the RSV promoter), which is diluted in culture medium (DMEM, 0.5% FCS). After approximately one hour at 37° C. in a moist atmosphere, the medium containing the adenoviral solution is aspirated off and replaced by culture medium (DMEM, 0.5% FCS) for a period of from 18 to 24 hours. The FCS-rich medium (final concentration of FCS: 20%) is then added in order to stimulate cell proliferation and the cells are counted 24 hours and 48 hours later.

In addition, at 24 hours after adding the adenoviral solution, expression of the GAX protein by the VSMCs is monitored by the techniques described in Example 2, namely nuclear labelling by means of immunofluorescence (localization of the protein) and also by western blotting. The protein produced by the recombinant adenovirus is efficiently detected by antibodies recognizing the HA epitope and possesses the same electrophoretic mobility as the GAX protein which is detected in the nucleus of VSMCs which are transferred with PCGNGAX or pXL-CMV-GAX$^{HA}$ FIG. 4 illustrates the location of the GAX protein in VSMCs which are incubated in the presence of Ad-CMVGAXHa.

Figure 4:
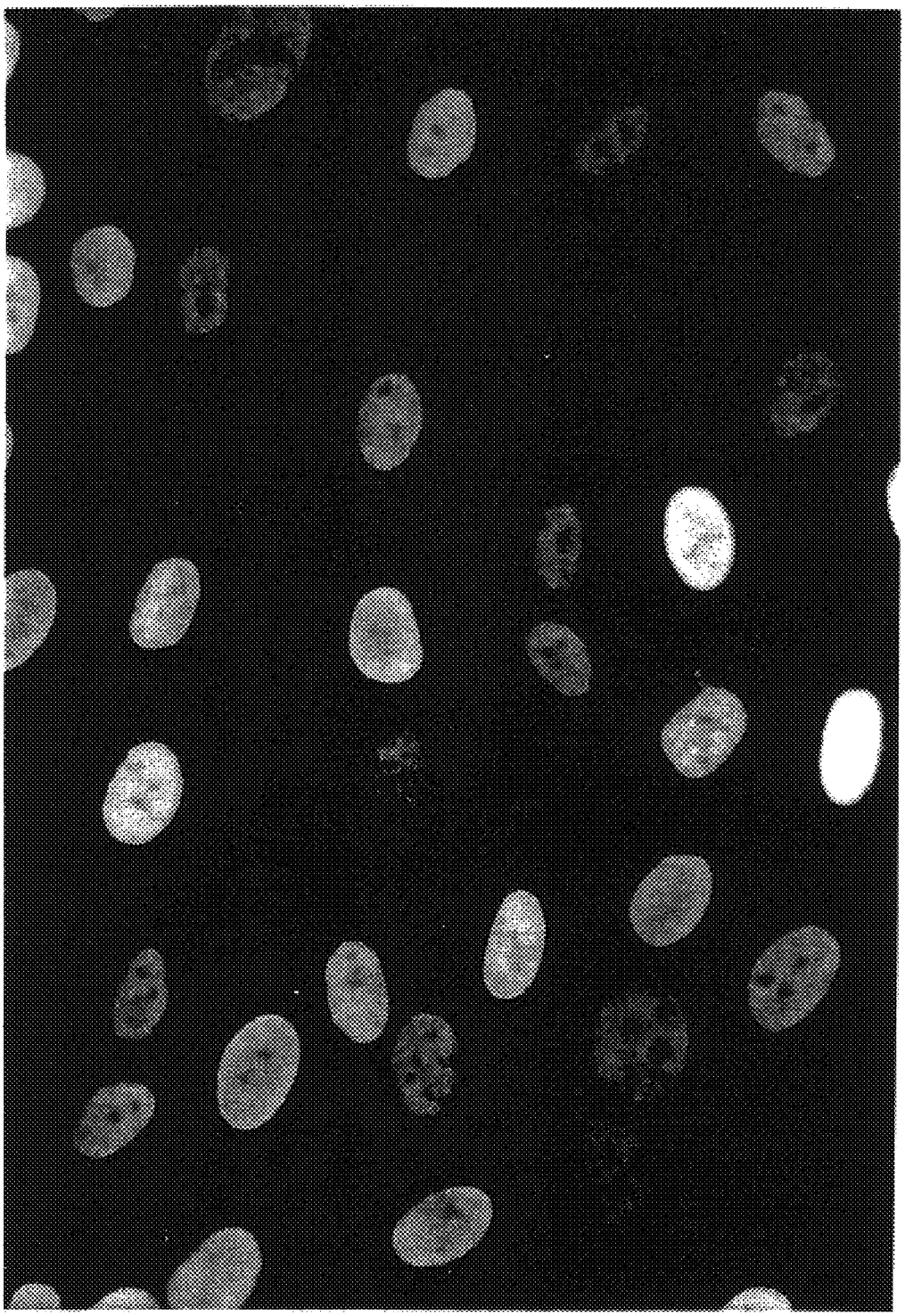
FIG. 4: Nuclear location of the GAX-HA protein in VSMCs treated with Ad-CMC-GAX.

The results of a representative experiment, which are shown in FIG. 4, demonstrate a marked fall in the number of cells following the addition of Ad-CMVGAXHA virus. On the other hand, this reduction in the number of cells is not observed following treatment with the control adenovirus used at the same concentration (M.O.I. 1000). We have verified in parallel, by means of immunofluorescence, that this high multiplicity of infection enables either the β-gal marker gene (use of anti-*E.Coli*. β-gal antibody, Monosan) or the GAX protein (use of anti-HA antibody, cf. Example 2) to be expressed in more than 90% of the rabbit VSMC population.

Figure 5:
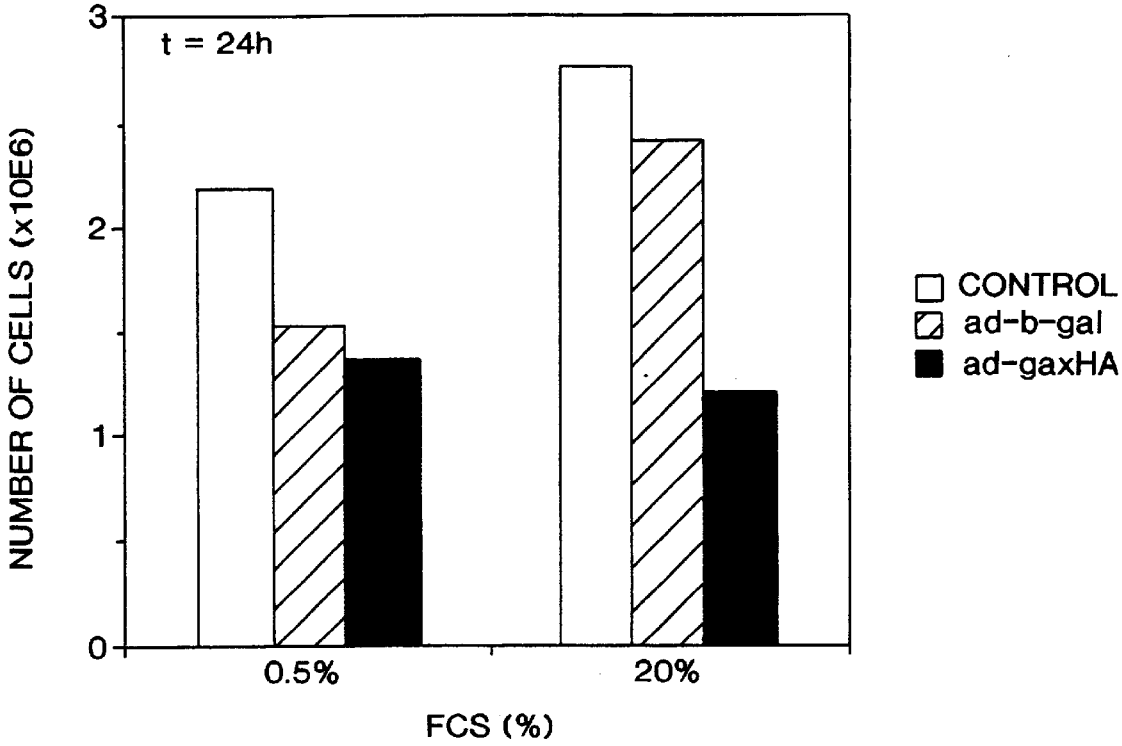
FIG. 5: Effect of Ad-CMV-GAX on the proliferation of VSMCs (t=24 hours)

Addition of ad-RSV gal virus is associated with a weak cytostatic effect (−13%) after culturing for 24 hours in the presence of foetal calf serum (20%). Under the same experimental conditions, the treatment with Ad-CMVGAXHA leads to a 57% decrease in the number of cells (cf. FIG. 5). The biological activity of the Ad-CMVGAXHa virus is very obviously accentuated after 48 hours of culture, and may even be associated with cell death (cf. FIGS. 6 and 7). Interestingly, this effect of Ad-CMVGAXHA is observed in cells which are stimulated with a high concentration of FCS (20%) but not in cells which are deprived of FCS (0.5%) (cf. FIG. 6). The effect of the Ad-CMVGAXHA adenovirus on the viability of VSMCs in culture is also illustrated by FIG. 7.

The inhibitory properties of Ad-CMVGAXHA on the synthesis of DNA are confirmed by bromodeoxyuridine (BrdU)-incorporation experiments. Briefly, at 24 hours after having added adenovirus, the VSMCs are incubated in the presence of FCS (10 to 20% and BrdU (10 μM), which is incorporated instead of thymine into the cells in the DNA synthesis phase and can be detected with specific antibodies. The BrdU incorporation is quantified by means of flow cytometry.

The same flow cytometry methodology can be employed for visualizing the progress made by Ad-CMVGAXHA-treated rabbit VSMCs in their cell cycle. Treatment with Ad-CMVGAXHA is accompanied by blockage of the cell cycle in the G0/G1 phase.

EXAMPLE 5

In Vivo Inhibition of intimal hyperplasia using an adenovirus-GAX

This example shows the efficacy of recombinant adenoviruses in a model of vascular pathology.

The model of arterial lesion used involves an abrasion of rat carotid (Clown et al., Lab Invest 49 (1983) 327–333). In this model, VSMCs dedifferentiate, proliferate and migrate to form a neointima that can partially occlude the artery within two weeks of the injury.

Sprague-Dawley rats were anesthesized by intraperitoneal injection of pentobarbital (45 mg/kg). Following external carotid arteriotomy, rat carotid arteries were denuded with a balloon catheter and exposed to $1.10^9$ pfu of Ad-CMVGAXHA or Ad-RSVβ-Gal. The adenovirus is used in a solution containing 15% poloxamer 407, which facilitates the adenovirus gene transfer. Following a twenty minute incubation, the virus solution was withdrawn and the ligatures were removed to restore circulation. Rats were sacrificed two weeks later and quantitative morphometric analyses were performed on cross sections of the treated vessels. The results are presented in FIGS. 8 and 9.

The results obtained show that all nine Ad-RSVβ-Gal transfected carotid arteries had a strong VSMC proliferation and developed considerable neointimal thickening. The area of the neointima was 0.186±0.02 $mm^2$ (SEM) with a range of 0.10 to 0.28. Luminal patentency was correspondingly narrowed by 40±4% (range 21 to 63), FIG. 8C. The intima-:media ratio was 1.51±0.1 (range 0.87 to 2.17). These results are similar to those obtained previously in saline treated control vessels. In contrast, Ad-CMVGAXHA treatment markedly reduced the pathologic response to balloon injury. For the Ad-CMVGAXHA treated vessels, mean area of neointimal lesion was 0.076±0.02 $mm^2$ (range 0 to 0.19), luminal narrowing was reduced to 17.5±5%. Statistical analysis confirmed that Ad-CMVGAXHA treatment significantly inhibited the development of intimal thickening relative to the Ad-RSVβ-Gal controls. Specifically, treatment with Ad-CMVGAXHA deceased the intima:media ratio by 69%, the intimal area by 59% and the luminal narrowing by 56% (FIGS. 8A and 8B). The remarkable effect on intimal hyperplasia is further emphasized by comparing the appearance of cross sections of control (FIG. 9A) with that of treated (FIG. 9B) animals.

This example demonstrates the very efficient in vivo growth arrest activity of the Ad-CMVGAXHA construct. This activity is very specific and not observed in control animals. The results presented clearly show the therapeutic activity of the Ad-CMVGAXHA on vascular morphology, and in particular, on hyperplasia which is associated with post-angioplasty restenosis.

EXAMPLE 6

GAX Expression Modulates the Injury-Induced Remodeling of Rabbit iliac Arteries in a Clinical Model of Balloon Angioplasty This example demonstrates that percutaneous GAX adenovirus-mediated gene transfer into injured non-atheromatous rabbit iliac arteries prevents neointimal formation and luminal narrowing without affecting reendothelialization or endothelium-dependent vasomotor responses.

Recombinant Adenoviral Vectors

Replication-defective recombinant adenoviral vectors, based on human adenovirus 5 serotype, were produced as described above and in Quantin et al. [*Proc Natl Acad Sci USA* 1992; 89:2581–2584] Stratford-Perricaudet et al. [*J. Clin. Invest.* 1993; 90:626–630] and Rosenfeld et al. [*Cell* 1992; 68:143–155].

Figure 1:
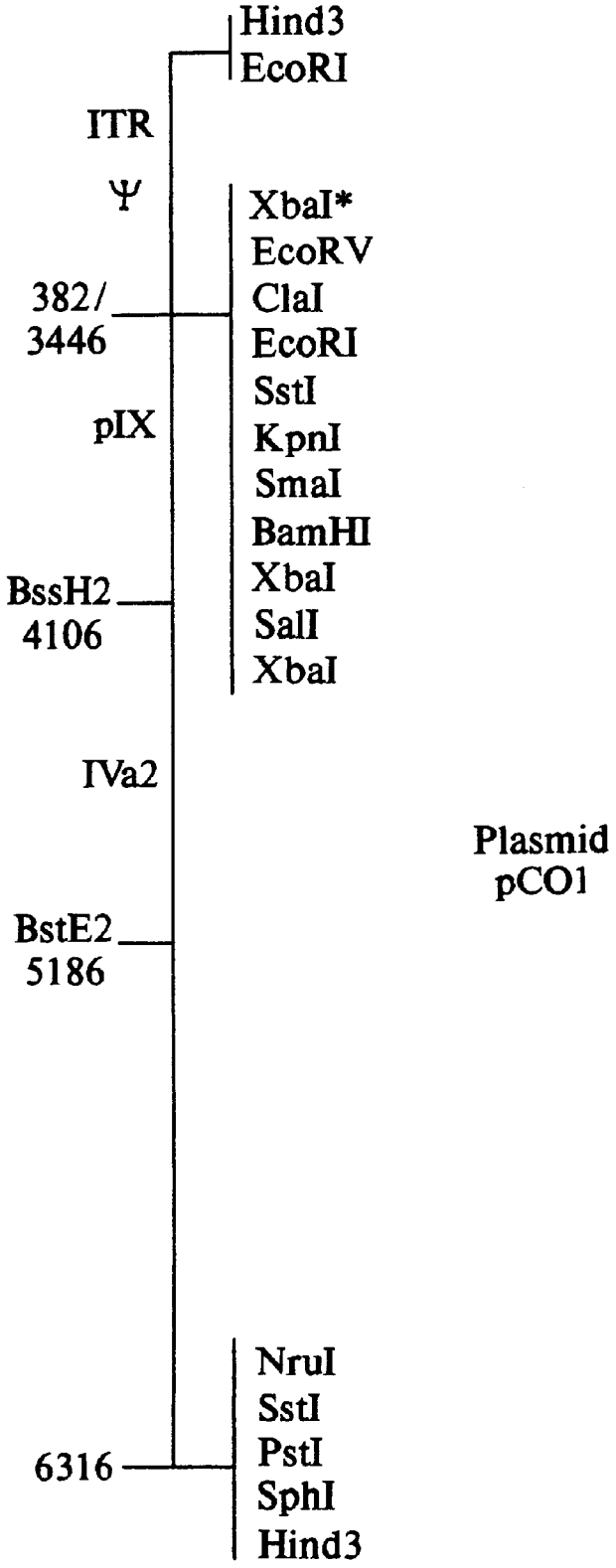
FIG. 1: Depiction of the plasmid pC01.

Percutaneous arterial gene transfer and balloon angioplasty in vivo:

New Zealand White rabbits (3.0–3.5 kg) (Pine Ace Rabbitry, Norton, Mass.) were anesthetized with ketamine (10 mg/kg) and acepromazine (0.2 mg/kg) following premedication with xylazine (2 mg/kg). In each rabbit, a 2.0 cm long, Channel balloon catheter (Boston Scientific, Watertown, Mass.) was introduced via the right common carotid and used to perform balloon angioplasty and arterial gene transfer. This catheter incorporates a conventional, 20 mm-long, polyethylene teraphalate balloon covered by a layer of 24 perforated channels which are perfused via an independent lumen (FIG. 1). This design is intended to permit low-pressure, local drug delivery simultaneous with high-pressure, balloon angioplasty [Riessen et al. *J. Am. Coll. Cardiol.* 1994; 23:1234–1244]. Balloon diameter was chosen to approximate a 1.3 to 1.5:1.0 balloon/artery ratio based on caliper measurement of magnified angiographic frames.

The angioplasty catheter was advanced to the lower abdominal aorta using a 0.014 in. guidewire (Hi-Torque Floppy II, Advanced Cardiovascular Systems, Temecula, Calif.) under fluoroscopic guidance, after reference angiogram following 200 βg of nitroglycerin. The balloon catheter was then advanced into one iliac artery immediately distal to the bifurcation between the external and interval iliac arteries where it was positioned using angiographic landmarks. Balloon inflation was then performed 3 times for 1 min each at 6 atm. The catheter was then inflated at nominal pressure and 200 μl of viral solution was instilled through the infusion port of the catheter. Infusion time was 60 sec. After 30 min incubation, the balloon was deflated and the catheter was removed.

In each animal, each iliac artery was randomly assigned to be treated with either AdCmv-GAX ($4\times10^9$ pfu) or the nlslacZ gene (AdRSV β-gal 4x109 pfu) (Group 1, n=9), or either AdRSV β-gal or saline (Group 2, n=8. For each rabbit, after completion of transfection of one iliac artery, the contralateral iliac artery underwent balloon injury using a new balloon. Before procedure, heparin sodium (200 USP units, Elkins-sinn, Cherry Hill, N.J.) were administered infra-arterially to prevent acute occlusion of the balloon-injured sites. All animals received aspirin in water approximately 50 mg daily, 3 days before procedure till the sacrifice.

In vivo vasomotor reactivity

Vasomotor reactivity of the arterial segment subjected to balloon angioplasty and arterial gene transfer was evaluated on the day of sacrifice. A 3 Fr., end-hole infusion catheter (Tracker-18™, Target Therapeutics, San Jose, Calif.) was inserted into the left carotid artery and advanced to the origin of transfected iliac artery using a 0.018 in. guidewire (Hi-Torque Floppy II) under fluoroscopic guidance. This catheter was used both for infusion of vasoactive drugs and selective angiography of the iliac artery. Angiography was performed first immediately before and after each drug administration using 1 ml of non-ionic contrast media (Isovue-370, Squibb Diagnostics, New Brunswick, N.J.). Serial angiographic images were recorded on 105-mm spot film at a rate of 2 films per sec. for 4 sec.

To assess endothelium-dependent vasomotor reactivity, acetylcholine chloride (Ach) and serotonin creative sulfate (5-HT) were delivered from a constant infusion pump (1 ml/min) via the 3 Fr. catheter at doses of 5 μg/kg/min, each for 2 min. Five min was allowed to elapse between each dose of agent to re-establish basal blood flow conditions. After administration of Ach and 5-HT respectively were completed, an identical protocol was employed to evaluate the contralateral artery. Finally, a single infra-aorta 200 μg of nitroglycerin was administered to assess endothelium-independent vasodilatation. The extent of the tone response was calculated as a percent of the maximal lumen diameter induced by nitroglycerin.

Ach, 5-HT were obtained from Sigma Chemical Co., St. Louis, Mo., and nitroglycerin from SoloPak Laboratories, Franklin Park, Ill. Fresh stock solutions of each were prepared immediately before each experiment.

Quantitative angiography

The angiographic luminal diameter of the iliac artery prior to gene transfer and prior to and after drug infusion, was determined using an automated edge-detection system [LeFree et al. *Proc SPIE* 1986; 626:334–341; Mancini et al. *Circulation* 1987; 75:452–460]. Each balloon-injured site was defined and the boundary lines were drawn according to the pilot angiogram of angioplasty balloon injury. The angiogram selected for analysis was scanned with a high resolution video camera; the signal produced by the video camera was digitized cad displayed on a video monitor Center-lines were traced manually for a 20 mm-long segment defined by the boundary lines drawn previously. Contours were detected automatically on the basis of the weighted sum of first and second derivative functions applied to the digitized brightness information. The average angiographic luminal diameter was then determined for the defined 20 mm-long segment.

Animal sacrifice

Thirty minutes prior to sacrifice, all rabbits received an intravenous injection of 5 ml 0.5% Evens blue dye (Sigma) [Clowes et al. *Lab Invest* 1978; 39:141–150] delivered via the ear vein to identify the remaining non-endothelialized area. A cannula was inserted into the lower abdominal aorta and used to perfuse a total of 100 ml of 0.9% saline solution with 10 units/ml heparin in situ, followed by 100 ml of 100% methanol. The baseline angiogram recorded prior to balloon injury and the pilot radiographic recording of the angioplasty balloon were used to identify the arterial segment to be harvested. The initially injured 2-cm long segment of iliac artery was then dissected free and incised longitudinally. The harvested arterial segment was pinned to a cork board, further fixed in 100% methanol, and photographed using a dissecting microscope (STEMI SR, Zeiss, Germany) in preparation for planimetric analysis of reendothelialization (see below). Tissues were further fixed by immersion in 100% methanol, embedded on longitudinal edge in paraffin, and cut in 5-$\mu$m sections onto slides coated with 3-aminopropyl-triethoxy-silane.

Tissue samples from liver, spleen, brain, testis, heart, lungs, ileun and kidneys were also systematically retrieved and immediately frozen in liquid nitrogen from the 9 GAX transfected rabbits of group one and those tissues from 3 randomized rabbits were analyzed for GAX expression at 1 month using RT-PCR (See below)

Planimetric analysis of re-endothelialization

Planimetric analysis was performed using the photograph of the harvested arterial segment taken through the dissecting microscope. The area of the intimal surface which was stained blue following application of Evans blue dye was interpreted to identify the portion of the arterial segment which remained endothelium-deficient. A computerized sketching program (MacMeasure version 1.9; NIMH, Bethesda, Md.) interfaced with a digitizing board (Summagraphics, Fairfield, Conn.) was used to outline the Evans blue positive and negative areas respectively. Specifically, the extent of endothelialized area was calculated as a percent of the total intimal area encompassed within the 2-cm length of artery.

Evaluation of intimal hyperplasia

Longitudinal histologic sections obtained from the 20 mm-length of injured artery and stained with an elastic tissue trichrome stain were projected onto the digitizing board, and the area of the intima and media respectively were measured using the computerized sketching program described above.

The thickness of the native media of the artery wall is variable reflecting in part the dimensions (diameter) of the individual rabbit iliac artery Accordingly, thickness of the media was used to index the extent of neointimal thickening, and is thus stated as the ratio of intima to media area (I/M).

Analysis of gene expression

Five animals were investigated 3 days after injury/local delivery into both iliac arteries with either AdGAX on one side or saline as control in the other side. Expression of GAX gene into the arterial wall and detection of remote localization was evaluated using reverse transcription-polymerase chain reaction RT-PCR). Transfected vessels, contralateral non-transfected vessels and tissue samples from liver, spleen, brain, testis, heart, lungs, ileun and kidneys were retrieved and immediately frozen in liquid nitrogen. Tissue samples were also systematically retrieved from the 9 GAX transfected rabbit of group one and those tissue from 3 randomized rabbits were analyzed.

RNA was extracted from tissues using the Ultraspec™ RNA system. Reverse transcription and DNA amplification were carried out in a thermal cycler (MJResarch, PTC-100) with oligodeoxynucleotide primers designed to amplify Ad-GAX DNA selectively over endogenously GAX gene. To facilitate this, the sense primer was designed to anneal to the epitope found in the adenoviral sequence while the antisense primer anneal to the protein coding region of GAX (5'-CCTTATGACGTGCCTGACTATGCC-3' (SEQ ID No. 2) and 5'-TGTGATGCTGGCTGGCAAACATGC-3' (SEQ ID No. 3) respectively). In each set of experiments, 1 $\mu$g of total RNA was denatured at 65° C. for 10 min. the then proceeded with the reverse transcription which was carried out at 42° C. for 15 min. denatured at 99° C. for 5 Min, and finally cooled at 5° C. for 5 min. The ensuring PCR reactions were performed: a hold at 95° C. for 105 sec, 35 cycles of 95° C. for 15 sec, 60° C. for 30 sec, then a final extension at 72° C. for 7 min. Amplification products were detected on 2% agarose gels stained with ethidium bromide. When RT-PCR was performed on tissue and on positive control as plasmid DNA containing the GAX rat gene used for the preparation of the adenoviral vector, a 238-bp DNA fragment was amplified from those tissues which expressed the Ad-GAX. RNA extractions and DNA amplifications were performed simultaneously and in duplicate for studied tissues and positive controls.

Statistical analysis

All results are expressed as means standard error (m±SE). Statistical significance was evaluated using a two tails paired Student's t test for comparisons between two means in the same animal. A value of $p<0.05$ was interpreted to denote statistical significance.

RESULTS

A total of 44 iliac arteries from 22 rabbits were analyzed in this study. Nine animals (group 1) underwent bilateral balloon injury and randomized transfection with Ad-GAX in one iliac artery and with Ad-β-gal in the other artery using a channel balloon catheter. Under identical conditions, a second group of 8 animals underwent bilateral injury and opposing arteries received either Ad-β-gal or saline. Iliac arteries were examined one month later for I/M ratio, lumen diameter, functional vasomotion and reendothelialization. Five additional animals were sacrificed at 3 days post-infection for the purpose of analyzing GAX gene an expression in the arterial wall and other tissues.

Neointimal thickening

The effect of Ad-GAX and Ad-β-gal on neointimal thickening was evaluated by light microscopic examination and quantitative morphometric analyses on longitudinal sections (FIG. 10). The Ad-GAX treated arteries had intimal area to medial area (I/M) ratios that were 50% less than the I/M ratios in the contralateral Ad-β-gal treated arteries (Ad-GAX=0.35±0.15; Ad-β-gaL=0.80±0.18; $p<0.02$) (FIG. 11). In contrast no statistically significant differences between the Ad-β-gal and the contralateral saline treated animals was observed in the second group (Ad-β-gal=0.81±0.19; saline=0.84±0.21; p=ns).

Re-endothelialization

Planimetric analysis was performed with Evans blue dye to evaluate the extents of reendothelialization at 28 days post-injury (FIG. 12). In the group 1 animals no significant difference was seen between arteries infected with Ad-GAX or Ad-β-gal (Ad-GAX=50±11.6%5; Ad-β-gal=60.6±10.7%) (FIG. 13). Similarly, no differences were found in the group 2 animals comparing arteries treated with Ad-β-gal or saline (Ad-β-gal=59.8±6.9%; saline=61±5.5).

Angiographic analyses of lumen diameter

The impact of Ad-GAX and Ad-β-gal infection was also evaluated by angiographic luminal diameter measurements at baseline and after a maximum dilatation induced by nitroglycerin in both groups of animals at 28 days post-injury (FIG. 14). The Ad-β-gal-treated arteries were significantly more narrow (1.28±0.15 mm at baseline and 1.39±0.16 mm after nitroglycerin) than the corresponding Ad-GAX-treated arteries both at baseline and after dilation with nitroglycerin (1.72±0.13 mm at baseline and 1.84±0.14 mm after nitroglycerin) in the group 1 animals (p=0.006) (FIGS. 15A and 15B). No significant differences in luminal narrowing was detected in the second group between vessels treated with Ad-β-gal (1.43±0.1 mm at baseline and 1.49±0.1 after nitroglycerin) and saline (1.45±0.08 mm at baseline and 1.46±0.09 mm after nitroglycerin). Results expressed as percentage of reduction of lumen diameter relative to reference lumen diameter showed a highly significant difference between the vessels infected with Ad-GAX (14.6±6%) and Ad-β-gal (36.7±7%) in the first group of animals (p=0.005) (FIGS. 15C and 15D). In the second group of animals no significant difference detected between vessels treated with Ad-β-gal (26±3%) and saline (28±5%).

Vasomotor reactivity

Previous investigations of the reendothelialization process have demonstrated that restoration of anatomic integrity and recovery of physiologic function do not proceed simultaneously [Tanaka et al. *Circulation* 1993; 33:1788–1803; Shimokawa et al. *Circ Res* 1987; 61:256–270; Weidinger et al. Circulation 1990; 81:1667–1679]. Accordingly, we determined the vasomotor response to endothelium-dependent agonists using quantitative angiography. Consistent with previous studies of the balloon-injured rabbit iliac [Weidinger et al., 1990], rabbit iliac arteries treated bilaterally with Ad-GAX or Ad-β-gal (group 1) and with Ad-β-gal or saline (group 2) demonstrated persistent impairment in vasomotor response to the endothelium-dependent agents acetylcholine (FIGS. 16A and 16B) and serotonin (FIGS. 16C and 16D) at 28 days post-injury. No difference were found in the two sets of treated vessels in each group (Table 2).

TABLE 2 response to endothelium-dependent agonist expressed as % of reduction of lumen diameter to maximal lumen diameter induced by nitroglycerin as the date of sacrifice

| Treat- | Group 1 | | Group 2 | |
|---|---|---|---|---|
| ment | GAX | β-gal | β-gal | Saline |
| Ach | −23.3 ± 3.9* | 18.8 ± 2.6* | −24.3 ± 5.3† | −19.2 ± 4.1 |
| 5-HT | −32.9 ± 4.7** | −24.8 ± 6.6** | −34.3 ± 5.1†† | −29.6 ± 8.9 |

Ach: Acetylcholine chloride, 5-HT: Serotonin creatinine sulfate
*, **, ††, p= ns.

Detection of GAX gene expression and dissemination

Five animals were investigated 3 days after injury/local delivery into both iliac arteries with either AdGAX or saline (Table 3). The results of GAX gene transfer and dissemination using RT-PCR were examined. RNA transcripts specific for Ad-GAX were detectable in the treated arteries and in the liver and the spleen of 2 animals while finding no expression in any other tissues samples from contralateral non transfected vessels, liver, spleen, brain, testis, heart, lungs, small intestine and kidney (FIG. 17). One month following transfection, using the same protocol describe above, analysis of tissue samples from 3 of the group one animals did not disclose the presence of GAX RNA.

TABLE 3

Results from RT-PCR from the 5 rabbits examined at 3 days.

| rabbit (n) | treated artery | contra-lateral artery | heart | lung | liver | spleen | testis | ileum | brain | kidney |
|---|---|---|---|---|---|---|---|---|---|---|
| 1 | ++ | − | − | − | − | − | − | − | − | − |
| 2 | ++ | − | − | − | − | + | − | − | − | − |
| 3 | ++ | − | − | − | + | + | − | − | − | − |
| 4 | ++ | − | − | − | − | − | − | − | − | − |
| 5 | ++ | − | − | − | − | − | − | − | − | − |

Discussion

A channel balloon was utilized under conditions that mimic a balloon angioplasty procedure prior to its use to percutaneously deliver the adenoviral construct. Evidence of transgene expression was provided by RT-PCR analyses using primers designed to specifically amplify the exogenous transcript. Evidence for GAX transgene expression was detected in iliac arteries at the site of transduction, but not in the contralateral artery that received the adenovirus encoding β-galactosidase. Using the channel balloon catheter, dissemination of the virally-encoded GAX gene was detected in the liver and spleen of two of the 5 test animals 3 days following transduction. However no evidence of gene expression could be detected after 30 days.

Analyses of longitudinal tissue sections of the iliac arteries revealed a 50% reduction in intimal thickness the GAX-treated arteries relative to the β-galactosidase-treated arteries. In contrast, there was no discernible difference between the β-galactosidase-treated and saline treated arteries in the control group. These data indicate that GAX overexpression can inhibit the formation of neointima in response to vascular injury, and the effect of GAX overexpression compares favorably with recent results reported by others groups using adenovirus-encoded genes for a mutant of Rb in rat and porcine models [Chang et al. *Science* 1995; 267:518–522], the herpes virus thymidine kinase gene in rat and porcine models [Guzman et al. *Proc Natl Acad Sci USA*. 1994; 91:10732–10736], p21 in a rat model [Chang et al., 1995] and hirudin in a rat model [Rade et al. *Nature Medicine* 1996; 2:293–298]. Overall, the inhibition of the intima/media ratio by these agents ranged from 35 to 46%.

Quantitative angiography was performed to determine minimal lumen diameters of the GAX-treated and control arteries to analyze the effects of GAX overexpression on vessel morphology. GAX-treated vessels displayed significantly larger lumen diameters than the contralateral Ad-β-gal-treated vessels both in baseline angiograms and in angiograms performed under conditions of maximum dilation. In contrast, no differences were detected in the lumen diameters were detected between the Ad-β-Gal and saline treated animals.

Evans blue staining at 30 days revealed incomplete reendothelialization in all experimental groups. No significant differences were seen between the GAX-treated and the β-gal-treated vessels nor between the β-gal or the saline treated vessels. Previous investigations in a variety of animal models have demonstrated that restoration of anatomic integrity and recovery of physiologic function do not proceed simultaneously [Shimokawa et al. *Circ Res* 1987; 61:256–270; Tanaka et al. *Circulation* 1993; 33:1788–1803; Weidinger et al. *Circulation* 1990; 81:1667–1679]. Accordingly, we analyzed vasomotor reactivity following adenovirus mediated gene transfer or saline treatment. Consistent with previous studies of vasomotor reactivity in the balloon-injured rabbit iliac artery [Weidinger et al., 1990] control rabbits transfected with β-gal demonstrated persistent impairment in response to Ach and 5-HT at four weeks post-injury. No differences in these parameters were detected in the GAX-treated vs. the β-gal-treated arteries nor between the saline- and β-gal treated vessels.

These data demonstrate that overexpression of the GAX gene in normal mammalian iliac arteries, more specifically rabbit iliac arteries, following endothelial denudation and arterial wall injury in a clinical model of balloon angioplasty prevents both neointima hyperplasia formation and luminal stenosis but does not affect reendothelialization and endothelium dependent vasomotion.

The use of a viral vector, such as an adenovirns to transfer the GAX gene in vivo is particularly efficient. This method is unique in that it combines both delivery efficiency and a therapeutic gene displaying two therapeutic properties: growth arrest and constitutive expression in a vascular system. The GAX gene transfer according to this invention induces a specific regression of hyperproliferative disorders in vascular vessels, thereby normalizing arterial functions. Local GAX gene transfer of the invention is also particularly advantageous in that it does not interfere with the reendothelization process following lesion of the artery. Furthermore, in addition to a direct impact on cell proliferation and vascular morphology, the GAX gene transfer according to the invention may also exert a beneficial indirect effect on the synthesis of extracellular matrix and on remodeling. It is believed that; the results obtained in animal models of GAX gene delivery correlate with the therapeutic benefit obtained in humans treated according to the invention. The results clearly show that GAX gene transfer according to the invention is a powerful new approach for the treatment of vascular lesions following angioplasty.

SEQUENCE LISTING

```
(1) GENERAL INFORMATION:

   (iii) NUMBER OF SEQUENCES: 3


(2) INFORMATION FOR SEQ ID NO: 1:

     (i) SEQUENCE CHARACTERISTICS:
          (A) LENGTH: 14 amino acids
          (B) TYPE: amino acid
          (C) STRANDEDNESS: <Unknown>
          (D) TOPOLOGY: linear

    (ii) MOLECULE TYPE: peptide

     (v) FRAGMENT TYPE: internal

    (xi) SEQUENCE DESCRIPTION: SEQ ID NO: 1:

Tyr Pro Tyr Asp Val Pro Asp Tyr Ala Ser Leu Gly Gly Pro
1               5                   10


(2) INFORMATION FOR SEQ ID NO: 2:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: other nucleic acid

   (iii) HYPOTHETICAL: NO

    (iv) ANTI-SENSE: NO
```

-continued

```
    (xi) SEQUENCE DESCRIPTION: SEQ ID NO: 2:

CCTTATGACG TGCCTGACTA TGCC                                          24


(2) INFORMATION FOR SEQ ID NO: 3:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: other nucleic acid

   (iii) HYPOTHETICAL: NO

    (iv) ANTI-SENSE: NO

    (xi) SEQUENCE DESCRIPTION: SEQ ID NO: 3:

TGTGATGCTG GCTGGCAAAC ATGC                                          24
```

We claim:

1. A method for inhibiting proliferation of mammalian vascular smooth muscle cells, said method comprising locally administering to said cells a replication defective recombinant adenovirus comprising a gene encoding a mammalian GAX protein, wherein said gene is expressed and proliferation of said cells is inhibited.

2. A method according to claim 1, wherein the adenovirus is of human or canine origin.

3. A method according to claim 2, wherein the adenovirus is a human Ad 5 or Ad 2.

4. A method according to claim 1, wherein the protein is a rat GAX protein.

5. A method according to claim 1, wherein the protein is a human GAX protein.

6. A method according to claim 1, wherein the inserted gene is a cDNA.

7. A method according to claim 1, wherein the inserted gene is a gDNA.

8. A method according to claim 1, wherein said adenovirus comprises a deletion of all or part of the E1 region.

9. A method according to claim 8, wherein said adenovirus additionally comprises a deletion of all or part of the E4 region.

10. A method according to claim 1, wherein the gene encoding the mammalian GAX protein is operably linked to a promoter.

11. A method according to claim 10, wherein the promoter is a viral promoter.

12. A method according to claim 11, wherein the viral promoter is a cytomegalovirus promoter.

13. A method according to claim 10, wherein the promoter is a tissue specific promoter.

14. A method according to claim 13, wherein the tissue is smooth muscle.

15. A method according to claim 10, wherein the promoter is an A method promoter.

16. A method according to claim 1, wherein said administering is to cells of a patient at risk of restenosis.

17. A method of inhibiting restenosis in a patient, said method comprising administering to vascular smooth muscle cells at a predetermined site in said patient a replication defective recombinant adenovirus comprising a gene encoding a mammalian GAX protein wherein said gene is expressed in vascular smooth muscle cells of said patient and inhibits proliferation of said cells.

18. A method according to claim 17, wherein said site is a site of mechanical injury to an arterial wall produced by treatment of an atherosclerotic lesion by angioplasty.

19. A method according to claim 18, wherein the adenovirus is administered with a balloon catheter.

20. A method according to claim 19, wherein the catheter is a hydrogel catheter.

21. A method according to claim 19, wherein the catheter is a perfusion balloon catheter.

22. A method according to claim 19, wherein the catheter is a channelled balloon catheter.

23. A method according to claim 17, wherein the adenovirus is of human or canine origin.

24. A method according to claim 23, wherein the adenovirus is a human Ad 5 or Ad 2.

25. A method according to claim 17, wherein the protein is a rat GAX protein.

26. A method according to claim 17, wherein the protein is a human GAX protein.

27. A method according to claim 17, wherein the inserted gene is a cDNA.

28. A method according to claim 17, wherein the inserted gene is a gDNA.

29. A method according to claim 17, wherein said adenovirus comprises a deletion of all or part of the E1 region.

30. A method according to claim 29, wherein said adenovirus additionally comprises a deletion of all or part of the E4 region.

31. A method according to claim 17, wherein the gene encoding the mammalian GAX protein is operably linked to a promoter.

32. A method according to claim 31, wherein the promoter is a viral promoter.

33. A method according to claim 32, wherein the viral promoter is a cytomegalovirus promoter.

34. A method according to claim 31, wherein the promoter is a tissue specific promoter.

35. A method according to claim 34, wherein the tissue is smooth muscle.

36. A method according to claim 31, wherein the promoter is an actin promoter.

*37. A method according to claim 2, wherein the adenovirus is a CAV2 adenovirus.*

*38. A method according to claim 1, wherein the replication defective recombinant adenovirus is administered in a dose of between about $10^4$ and about $10^{14}$ plague-forming units.*

*39. A method according to claim 38, wherein the replication defective recombinant adenovirus is administered in a dose of between about $10^6$ and about $10^{10}$ plaque-forming units.*

*40. A method according to claim 10, wherein the gene further comprises a signal sequence, which directs the GAX protein into a secretory pathway of a cell to which the replication defective recombinant adenovirus has been administered.*

*41. A method according to claim 4, wherein the gene encodes a fusion protein consisting of the HA1 epitope of an influenza virus haemagglutinin fused to the N-terminus of the rat GAX protein, and expression of the epitope can be used to monitor the expression of the GAX protein.*

*42. A method according to claim 3, wherein the GAX protein is a rat GAX protein.*

*43. A method according to claim 3, wherein the GAX protein is a human GAX protein.*

*44. A method according to claim 23, wherein the adenovirus is a CAV2 adenovirus.*

*45. A method according to claim 17, wherein the replication defective recombinant adenovirus is administered in a dose of between about $10^4$ and about $10^{14}$ plaque-forming units.*

*46. A method according to claim 45, wherein the replication defective recombinant adenovirus is administered in a dose of between about $10^6$ and about $10^{10}$ plaque-forming units.*

*47. A method according to claim 31, wherein the gene further comprises a signal sequence, which directs the GAX protein into a secretory pathway of a cell to which the replication defective recombinant adenovirus has been administered.*

*48. A method according to claim 25, wherein the gene encodes a fusion protein consisting of the HA1 epitope of an influenza virus haemagglutinin fused to the N-terminus of the rat GAX protein, wherein expression of the epitope can be used to monitor the expression of the GAX protein.*

*49. A method according to claim 24, wherein the GAX protein is a rat GAX protein.*

*50. A method according to claim 24, wherein the GAX protein is a human GAX protein.*

* * * * *